US007498566B2

(12) United States Patent
Kasper et al.

(10) Patent No.: US 7,498,566 B2
(45) Date of Patent: Mar. 3, 2009

(54) AUTOMATED QUALITY CONTROL MECHANISM FOR A NUCLEAR DETECTOR

(75) Inventors: Robert Kasper, Chicago, IL (US); Jeffrey A. Giannini, Algonquin, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 210 days.

(21) Appl. No.: 11/424,760

(22) Filed: Jun. 16, 2006

(65) Prior Publication Data

US 2006/0284065 A1 Dec. 21, 2006

Related U.S. Application Data

(60) Provisional application No. 60/691,325, filed on Jun. 16, 2005.

(51) Int. Cl.
*G01D 18/00* (2006.01)
*G12B 13/00* (2006.01)
(52) U.S. Cl. .................................. 250/252.1; 250/497.1
(58) Field of Classification Search ............ 250/363.04, 250/497.1, 252.1
See application file for complete search history.

(56) References Cited

U.S. PATENT DOCUMENTS

| 5,525,905 | A | * | 6/1996 | Mohapatra et al. ........... 324/318 |
| 5,691,538 | A | * | 11/1997 | Ohike et al. ............ 250/363.05 |
| 5,866,906 | A | * | 2/1999 | Jensen .................... 250/363.05 |
| 6,617,582 | B2 | * | 9/2003 | Stark ..................... 250/363.05 |
| 2007/0050908 | A1 | * | 3/2007 | Kogan et al. .................... 5/128 |
| 2007/0145257 | A1 | * | 6/2007 | Petrillo et al. ............. 250/252.1 |

* cited by examiner

*Primary Examiner*—Nikita Wells
*Assistant Examiner*—Johnnie L Smith, II
(74) *Attorney, Agent, or Firm*—Peter L. Kendall

(57) ABSTRACT

A quality control mechanism for a nuclear camera system having a field of view includes at least one source assembly for a radioactive material. The source assembly is configured to automatically remotely move the radioactive material into the field of view and automatically remotely move the radioactive material out of the field of view. The nuclear camera system may have a patient handling system. The quality control mechanism is integrated with the patient handling system at the front end. The radioactive material may be configured as a line source or a point source. A multiple head registration shield tube assembly may extend over the line source to substantially limit the radioactivity emitted by a number of slots in the shield tube assembly.

17 Claims, 19 Drawing Sheets

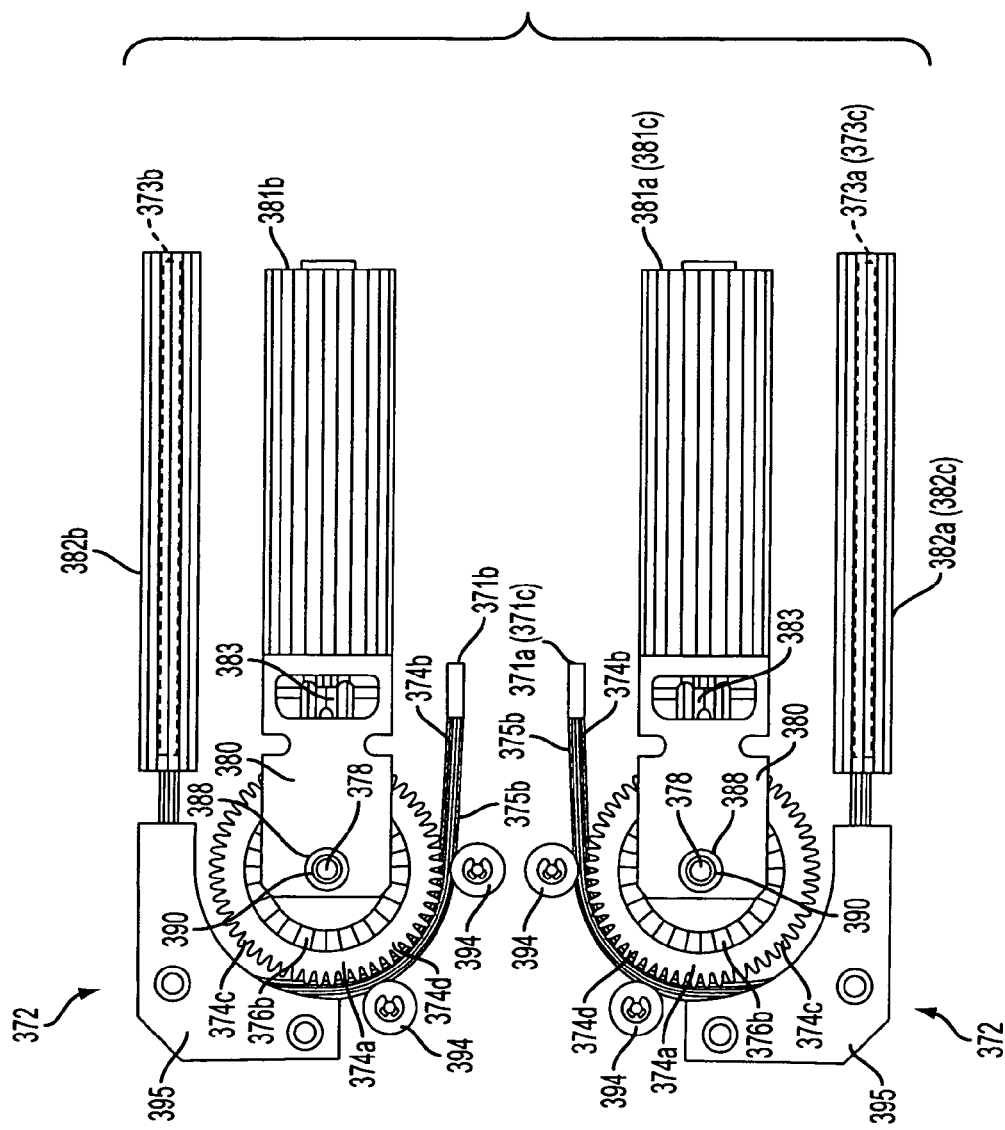

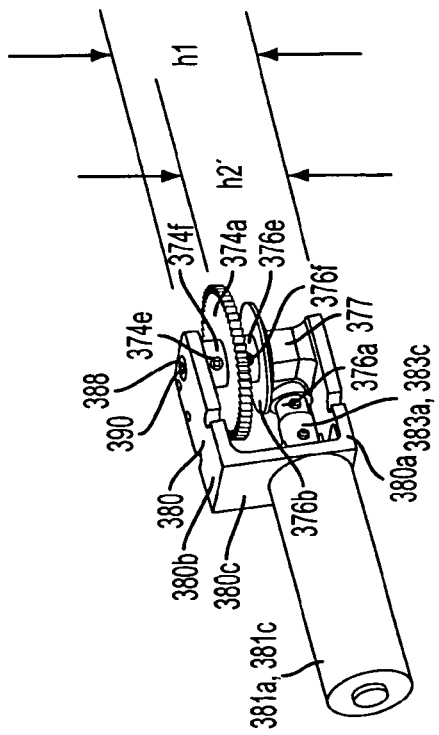
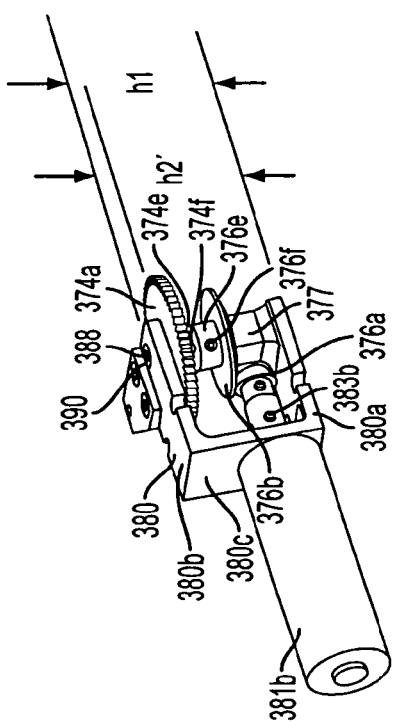
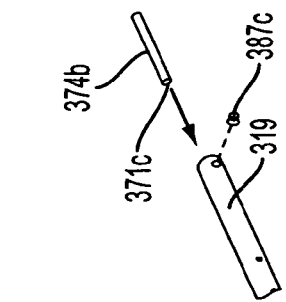
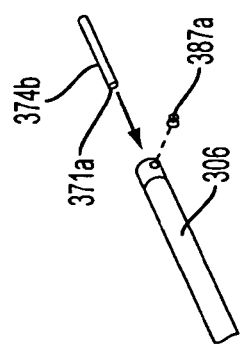
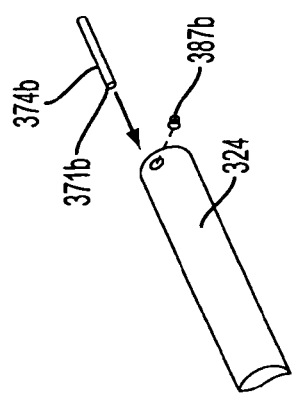

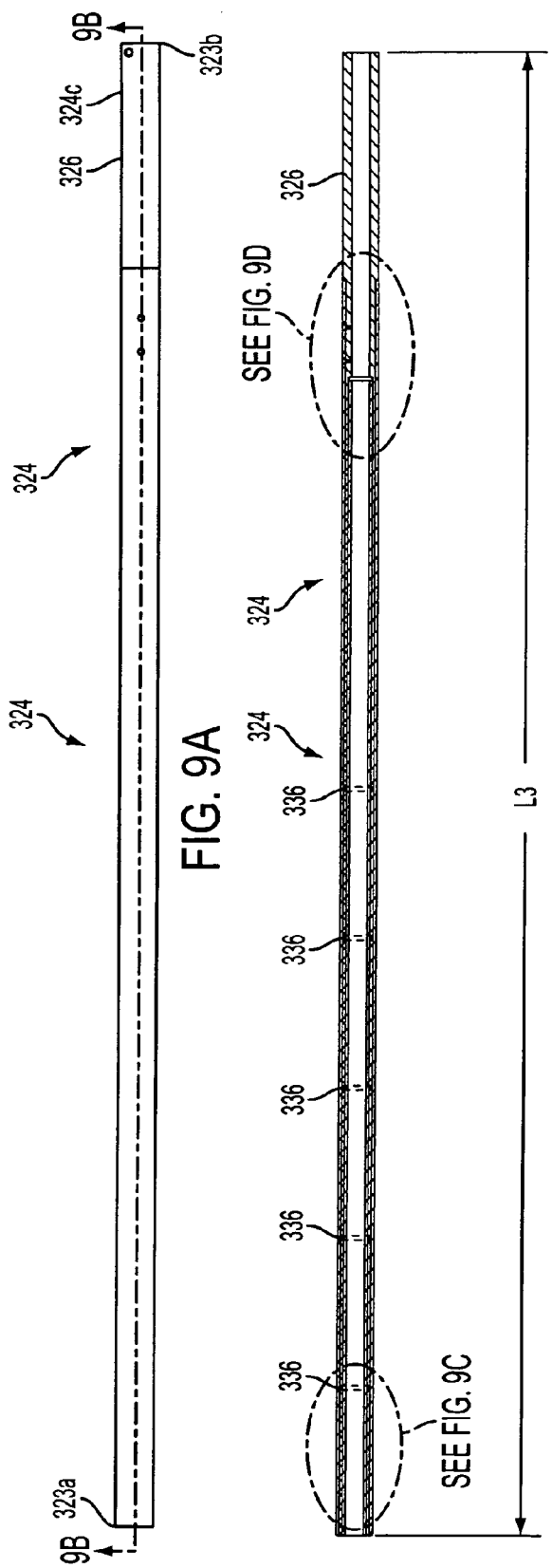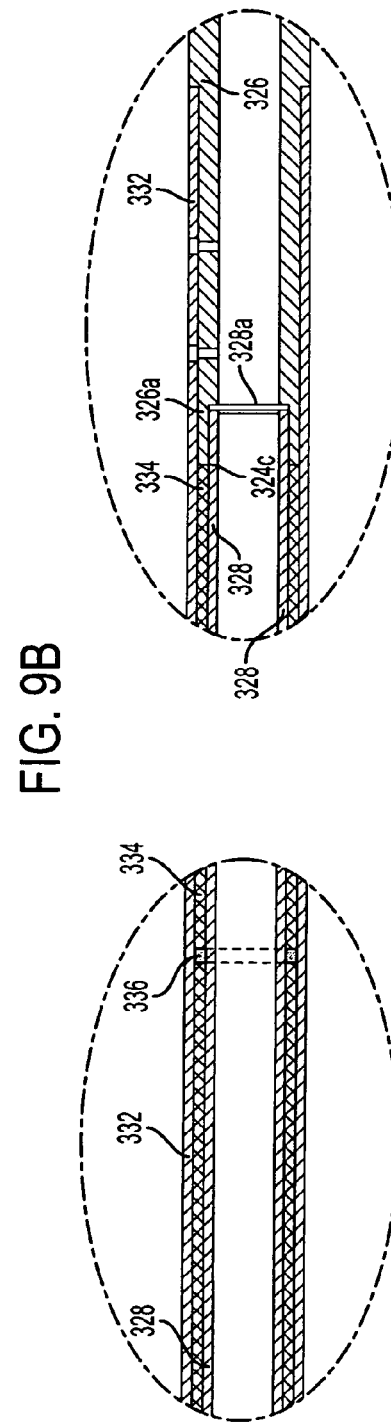

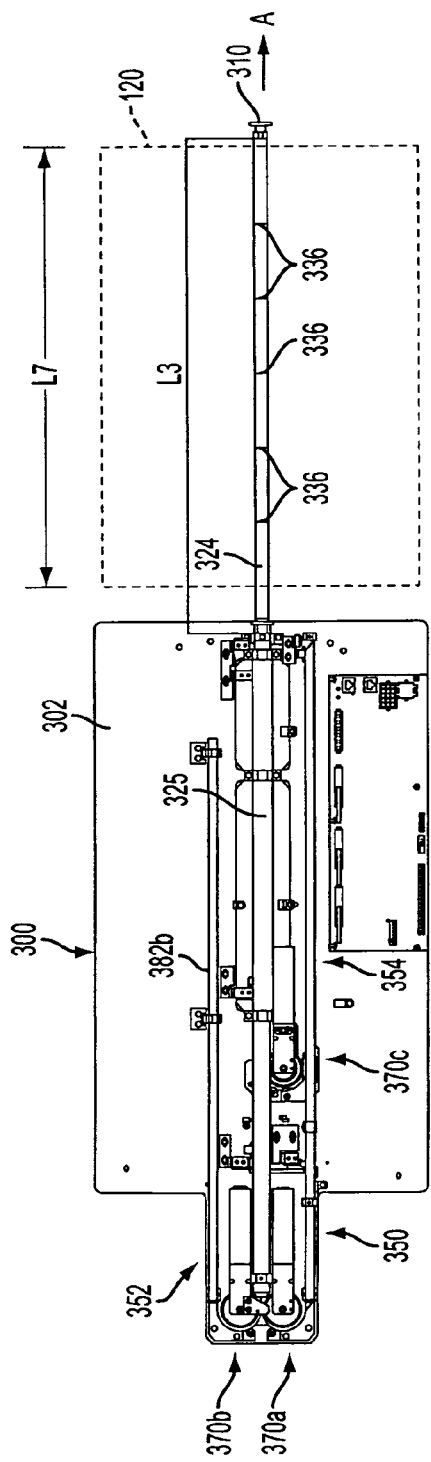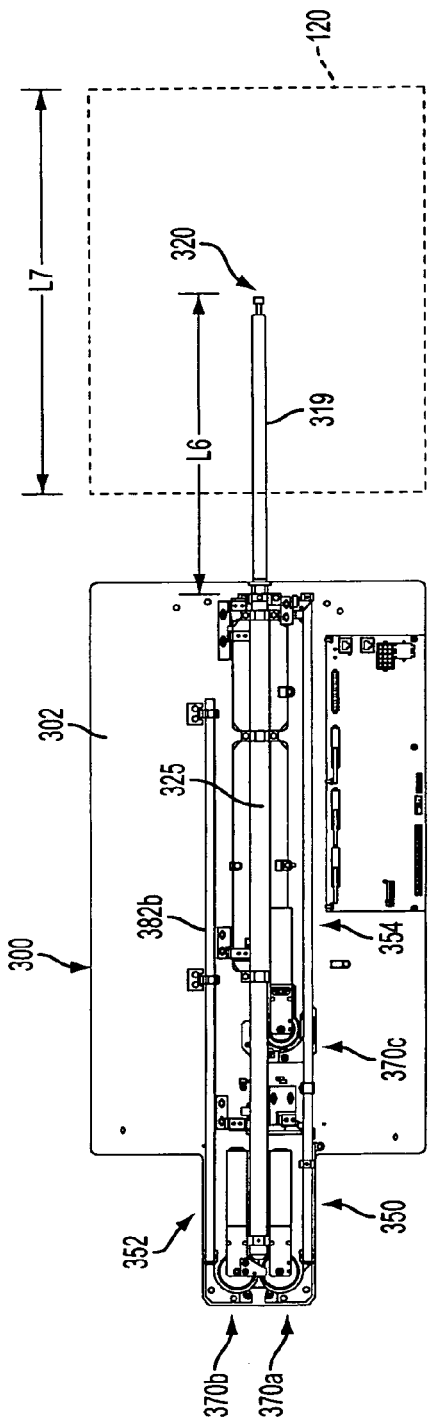
FIG. 14
FIG. 15

AUTOMATED QUALITY CONTROL MECHANISM FOR A NUCLEAR DETECTOR

CROSS-REFERENCE TO RELATED APPLICATIONS

This application claims the benefit of and priority to U.S. Provisional Patent Application Ser. No. 60/691,325 filed on Jun. 16, 2005, the entire contents of which is incorporated by reference herein.

BACKGROUND

1. Field of the Invention

The present invention generally relates to nuclear medicine and, more particularly, to systems and methods for obtaining nuclear medicine images of a patients body and/or organs of interest.

2. Description of the Background Art

Nuclear medicine is a unique medical specialty wherein radiation is used to acquire images which show the function and anatomy of organs, bones or tissues of the body. Radiopharmaceuticals are introduced into the body, either by injection or ingestion, and are attracted to specific organs, bones or tissues of interest. Such radiopharmaceuticals produce gamma photon emissions which emanate from the body. One or more detector heads are used to detect the emitted gamma photons, and the information collected from the detector head(s) is processed to calculate the position of origin of the emitted photon from the source (e.g., the body organ or tissue under study). The accumulation of a large number of emitted gamma positions allows an image of the organ or tissue under study to be displayed.

There are basically two types of imaging techniques, namely, positron emission tomography (PET) and single photon emission computed tomography (SPECT). Both PET and SPECT require gamma ray detector head(s) that calculate and store both the position of the detected gamma ray and its energy. Typically, detector head(s) include a scintillation plate which converts each received radiation event (e.g., the emitted gamma photons) into a scintillation or flash of light. An array of photomultiplier tubes positioned behind the scintillation plate and associated circuitry determine a coordinate location and a value of energy for each scintillation event.

The calibration and verification of the system is currently performed manually through the preparation and placement on the system of Tc-99m point source(s) and/or the placement of 5-20mCi Co-57 sheet source.

In that the goal of protection against undesired exposure to radioactivity is to reduce exposure to a level "as low as reasonably achievable" (ALARA), a need exists to reduce the daily exposure of the technologists to radiation relative to that received during current quality control (QC) procedures.

SUMMARY

A mechanism or system and method for calibration and verification of a nuclear camera system are disclosed.

The present disclosure relates to a quality control mechanism for a nuclear camera system having a field of view. The quality control mechanism includes at least one source assembly for a radioactive material wherein the at least one source assembly is configured with respect to the quality control mechanism in order to automatically remotely move the radioactive material into the field of view and automatically remotely move the radioactive material out of the field of view. The nuclear camera system may include a patient handling system having a front end and a rear end and the quality control mechanism may be integrated with the patient handling system at the front end such that the radioactive material can be at least one of automatically remotely extended into the field of view and automatically remotely retracted from the field of view. The at least one source assembly may be mounted on a mounting plate and the quality control mechanism may be integrated with the patient handling system via the mounting plate being mounted to the patient handling system. In one embodiment, the at least one source assembly may include a line source assembly having a line source incorporated therein, wherein the line source is a radioactive material. A line drive may be included for driving the line source, with the line drive being capable of at least one of extending the line source into the field of view and retracting the line source from the field of view. The quality control mechanism may further include a multiple head registration assembly configured with a plurality of slots formed therein and configured to extend over and shield the line source assembly such that the line source emits a field of radiation substantially only through the plurality of slots. In one embodiment, the at least one source assembly includes a point source incorporated therein wherein the point source is a radioactive material. The quality control mechanism may further include a point drive for driving the point source, the point drive being capable of at least one of extending the point source into the field of view and retracting the point source out of the field of view. The quality control mechanism may further include a shield cover configured to shield the radioactive material. In one embodiment, the line drive includes a flexible gear set having a drive gear, and a flexible gear rack interfacing with the drive gear. The flexible gear rack may be operatively connected to the line drive to enable at least one of the extension and retraction of the line source to and from the field of view.

In one embodiment, the point drive includes a flexible gear set including a drive gear, and a flexible gear rack interfacing with the drive gear. The flexible gear rack may be operatively connected to the point drive to enable at least one of the extension and retraction of the point source to and from the field of view.

The multiple head registration assembly may include a multiple head registration assembly shield tube, and a drive for driving the multiple head registration assembly, the drive including a drive gear, and a flexible gear rack interfacing with the drive gear. The flexible gear rack may be operatively connected to the multiple head registration assembly such that the plurality of slots can be extended over and shield the line source assembly such that the line source emits a field of radiation substantially only through the plurality of slots. The drive of the multiple head registration may include a bevel pinion gear interfacing with a bevel driven gear.

The envelope of the quality control mechanism may be defined by a height not greater than about 5.72 centimeters (about 2.25 inches), by a width not greater than about 15.24 centimeters (about 6 inches) and by a length not greater than about 83.8 centimeters (about 33 inches).

The present disclosure relates also to a method of calibrating a nuclear camera system having a field of view, with the method including the step of at least one of automatically remotely extending into the field of view and automatically remotely retracting from the field of view a radioactive material. The radioactive material may be configured as one of a line source and a point source. When the radioactive material is configured as a line source, the method may further include the step of extending a shield tube over the line source, with the shield tube including a plurality of slots formed therein such that the line source emits a field of radiation substantially only through the plurality of slits.

The above is a brief description of some deficiencies in the prior art and advantages of the present invention. Other features, advantages and embodiments of the invention will be apparent to those skilled in the art from the following description, drawings and claims.

BRIEF DESCRIPTION OF THE DRAWINGS

The invention will become more clearly understood from the following detailed description in connection with the accompanying drawings, in which:

FIG. 6B is a plan view of the drive assembly of FIG. 6A;

FIG. 6C is a perspective view of a portion of a flexible gear drive assembly for a multiple head registration (MHR) shield tube of the AQCM;

FIG. 6D is a perspective view of a portion of a flexible gear drive assembly for either a line source assembly or a point source assembly of the AQCM;

FIG. 6E is a perspective view of another portion of a flexible gear drive assembly for an MHR shield tube of FIG. 6C;

FIG. 6F is a perspective view of yet another portion of a flexible gear drive assembly for a line source assembly of FIG. 6D;

FIG. 6G is a perspective view of still another portion of a flexible gear drive assembly for a point source assembly of FIG. 6D;

FIG. 5C is an elevational view of the line source assembly of FIG. 5A with parts assembled;

FIG. 9A is a plan view of the multiple head registration (MHR) shield assembly of FIG. 9;

FIG. 9B is a cross-sectional view of the MHR shield assembly of FIG. 9A taken alone section line 9A-9A of FIG. 9A;

FIG. 9C is an enlarged view of a first area of detail of the MHR shield assembly illustrated in FIG. 9B;

FIG. 9D is an enlarged view of a second area of detail of the MHR shield assembly illustrated in FIG. 9B;

FIG. 14 is a plan view of the AQCM of the present disclosure with the MHR shield tube assembly in the fully extended position partially exposing the line source assembly in the field of view of a nuclear camera; and FIG. 15 is a plan view of the AQCM of the present disclosure with the point source assembly in the fully extended position in the field of view of a nuclear camera.

DETAILED DESCRIPTION OF THE EMBODIMENTS

The following description is presented to enable one of ordinary skill in the art to make and use the invention and is provided in the context of a patent application and its requirements. Various modifications to the preferred embodiments will be readily apparent to those skilled in the art and the generic principles herein may be applied to other embodiments. Thus, the present invention is not intended to be limited to the embodiment shown but is to be accorded the widest scope consistent with the principles and features described herein.

Figure 1:
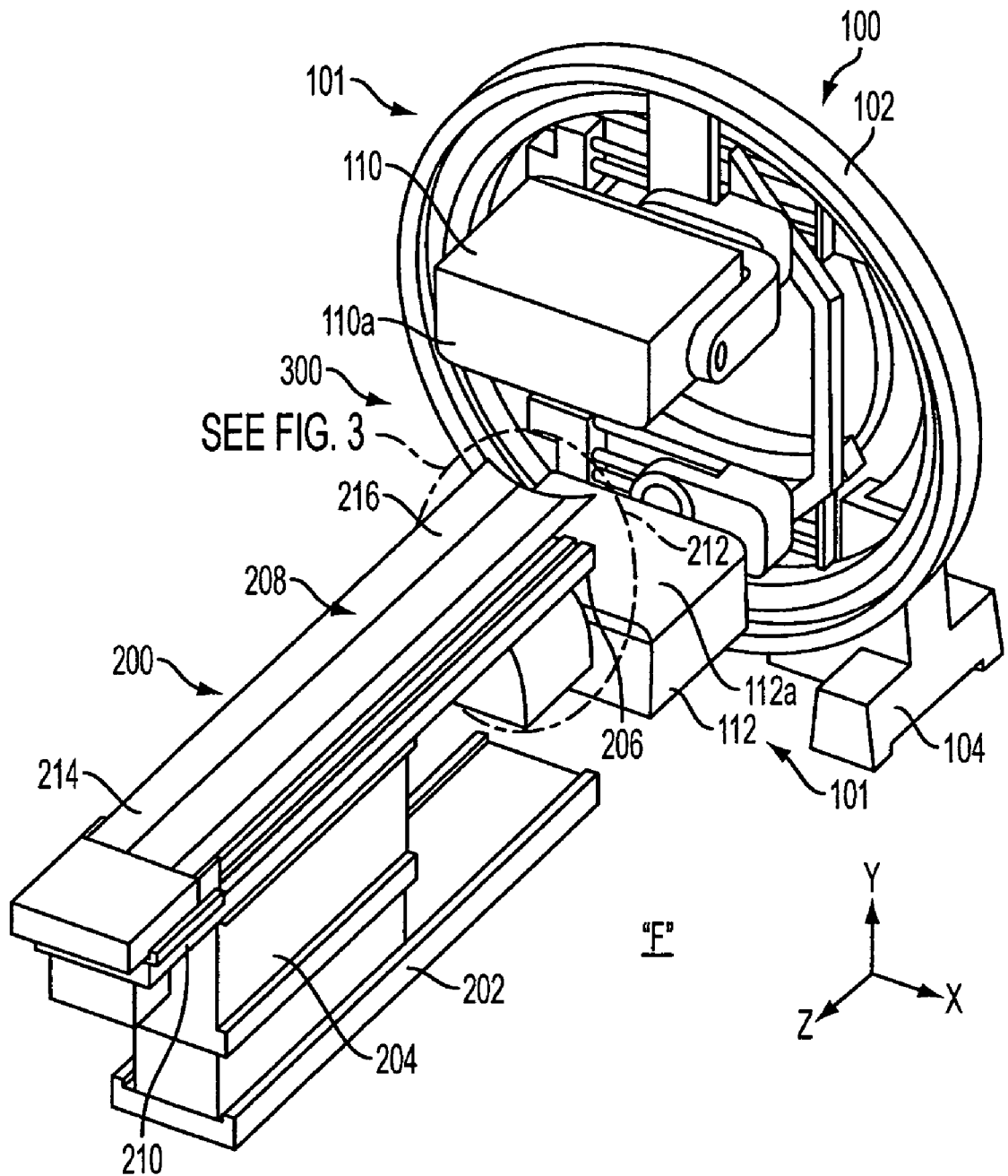
FIG. 1 is a top perspective view and partial schematic illustrating an example of a nuclear medicine gantry and patient handling system integrated with an automated quality control mechanism (AQCM) for calibration of a nuclear camera in accordance with the present disclosure.
Figure 2:
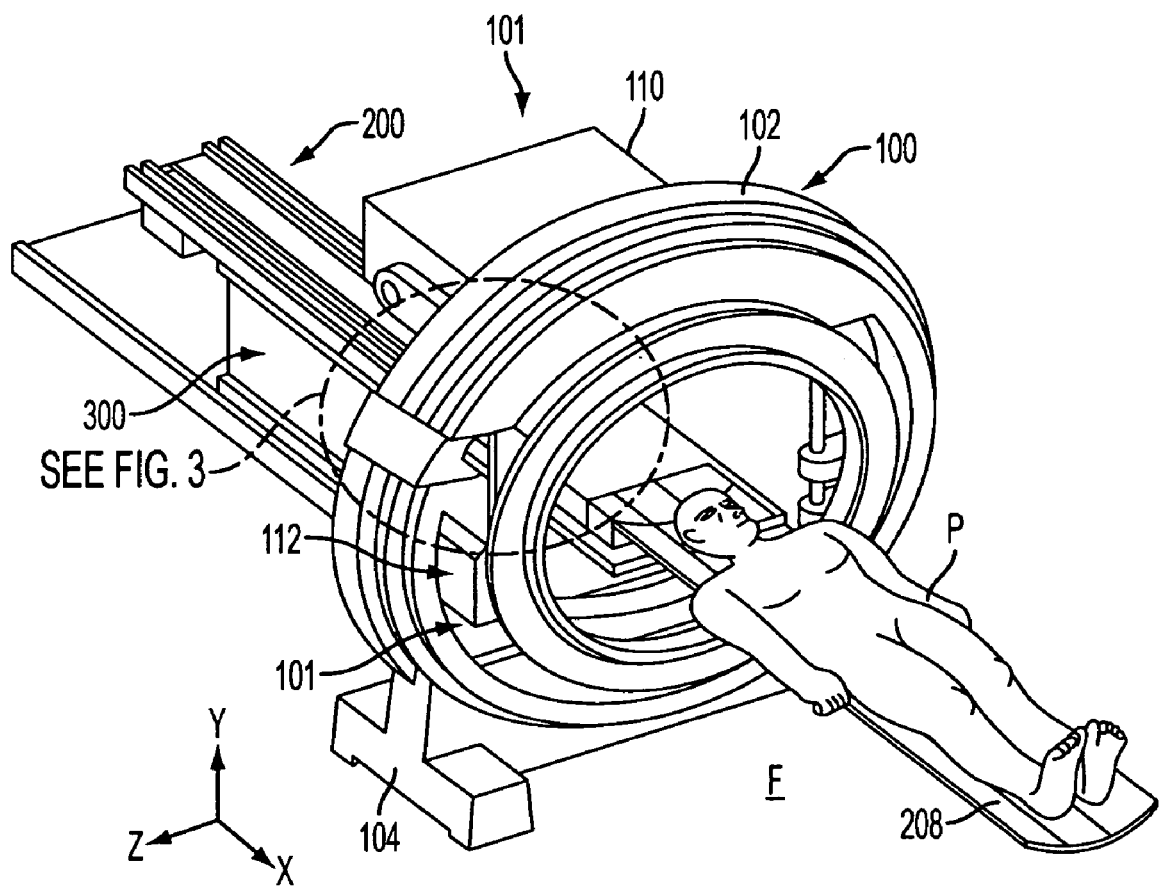
FIG. 2 is a rear perspective view and partial schematic of the nuclear medicine gantry and the patient handling system of FIG. 1, illustrating the positioning of a patient through the ring of the nuclear medicine gantry.
Figure 3:
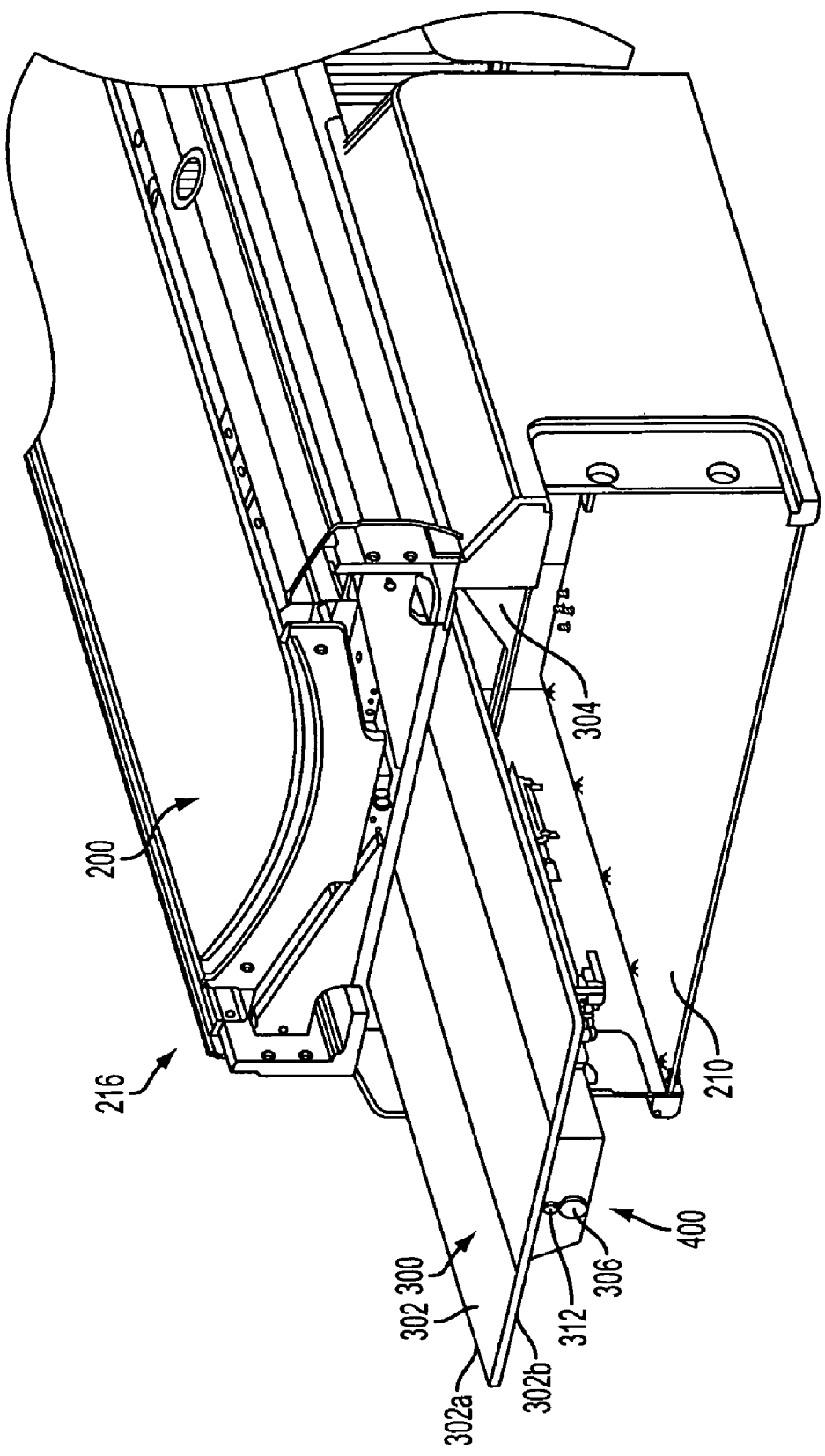
FIG. 3 is a top perspective view of the AQCM of the present disclosure as integrated with the patient handling system of the nuclear medicine gantry.

Referring now to the drawings, and initially to FIGS. 1-2, an example of a nuclear medicine gantry which may be integrated with an automated quality control mechanism for calibration of a nuclear medicine camera in accordance with the present disclosure is shown and generally indicated at 100. Such a nuclear medicine gantry is described in commonly-owned U.S. Patent Application Publication No. 2004/0262525 by Yunker et al., entitled "NUCLEAR MEDICINE GANTRY AND METHOD", the entire contents of which is incorporated by reference herein.

Nuclear medicine gantry 100 includes a ring 102 operatively connected to and supported on a stand 104. Ring 102 is supported on stand 104 in such a manner that a central longitudinal Z axis of ring 102 is oriented in a plane substantially parallel to floor "F". Ring 102 defines an X-Y plane.

Ring 102 defines an inner annular race (not shown) rotatable about the central longitudinal Z axis, including a series of teeth (not shown), in the form of a gear, along substantially the entire circumference of the inner annular race. In addition, stand 104 can be provided with a drive mechanism (not shown) including a gear, in the form of a pinion, which is configured and dimensioned to engage and cooperate with the teeth of the inner annular race. In this manner, rotation of the gear of the drive mechanism results in rotation of the inner annular race about the longitudinal Z axis as indicated by double-headed arrow "A" in FIG. 2. White one method of rotating the inner annular race about the longitudinal Z axis has been described, it will be readily apparent to those skilled in the art that other methods of rotating the inner annular race about the longitudinal Z axis can be provided.

Nuclear medicine gantry 100 further includes a first detector head 110 and a second detector head 112, each detector head 110, 112 being operatively associated with and/or mounted to ring 102. The first and second detector heads 110 and 112 form a portion of a nuclear camera system 101.

According to the present disclosure and as seen in FIGS. 1-2, by way of example, a patient handling system (PHS) 200 can be provided and can be integrated with the automated quality control mechanism (AQCM) 300 according to the present disclosure.

As will be described in more detail below, in one embodiment, the AQCM 300 operates by deploying from a shielded housing a 42 cm 10 mCi Co-57 line source or a 50 pCi Co-57 point source. Optionally, in one embodiment, a slotted shield may be extended over the line source to effectively convert the line source into a series of five evenly spaced points for the purpose of imaging. These source configurations are imaged by the system in set configurations for the purpose of calibrating the system detector performance and gantry alignment. The source configurations may also be deployed for the purpose of verifying the clinical performance of the system prior to daily use.

By automating the calibrating functions of the nuclear camera system 101 with a contained device, the daily exposure of the technologists to radiation should be reduced relative to that received during the QC (quality control) procedures of the prior art which are performed manually. In addition, the configuration of the AQCM 300 results in a low profile or reduced form factor that facilitates mounting to the patient handling system 200 and reduces the amount of radiation shielding that is required.

As seen in FIGS. 1 and 2, patient handling system 200 includes a lower frame 202 supported on floor "F", a lift mechanism 204 operatively supported on to lower frame 202, an upper frame 206 operatively supported on lift mechanism 204 and a pallet 208 translatably supported on upper frame 206. Patient handling system 200 is oriented such that pallet 208 is translatable in directions parallel to the longitudinal Z axis of ring 102. Lift mechanism 204 (e.g., parallelogram style, scissors style, etc.) provides the up and down motion of upper frame 206 and pallet 208 for patient loading and positioning. Upper frame 206 includes a rear end portion 210 operatively supported on lift mechanism 204 and a front end portion 212 extending from lift mechanism 204 in a direction toward nuclear medicine gantry 100.

Pallet 208 is configured and adapted such that a rear end portion 214 thereof is translatably supported on upper frame 206 and a front end portion 216 thereof is free floating. It is envisioned that bearing cars (not shown) may be mounted to a lower surface of pallet 208 to engage linear rails (not shown) that are fixed to an upper surface of upper frame 206. Translation of pallet 208 relative to upper frame 206 is achieved through a screw drive and/or a belt drive (not shown).

Referring now to FIGS. 3-15, an embodiment of the AQCM 300 of the present disclosure is designed and assembled as a self-contained mechanism. The AQCM 300 is integrated within and operatively associated with the PHS 200 to perform automated quality control of the nuclear camera system 101. More particularly, referring to FIGS. 3-7, the AQCM 300 includes a mounting plate 302, having, in one embodiment, a generally planar profile. Mounting plate 302 includes a first surface 302a and a second surface 302b, wherein in one embodiment, the first and second surfaces 302a and 302b may be generally planar and on opposite sides of one another. The mounting plate 302 is insertable into an aperture 304 formed at the rear end portion 210 of the PHS 200.

As illustrated in FIGS. 4 and 8A-8C, and as discussed in more detail below, the AQCM 300 includes a line source assembly 306 having a radioactive line source 308 and a line source shielding plug 310 secured to an end of line source 308. In one embodiment, line source 308 may have a substantially cylindrically-shaped cross-section and have an active length L1 (see FIG. 8A). In one embodiment, line source 308 may be cobalt-57 (Co-57) having an activity of 10 millicuries (10 mCi). The line source 308 is contained within a line source holder tube 308a. The line source holder tube 308a has a length L2 (see FIG. 8A).

Turning now to FIGS. 4, 5, 5A and 9 to 9G, the AQCM 300 also includes a multiple head registration (NMR) shield 329 which includes a hollow MHR shield assembly support tube 325 having a front end 325a and a rear end 325b and having a bore hole 325c formed therein. The MHR shield 329 also includes an MHR shield tube assembly 324 disposed within bore hole 325c of MHR shield assembly support tube 325. MHR shield tube assembly 324 includes an outer shield tube 332, a middle shield tube 334 concentrically disposed within outer shield tube 332, and an inner shield tube 328 concentrically disposes within middle shield tube 334. As seen in FIG. 9D, middle shield tube 334 has a length that is shorter than outer shield tube 332, and inner shield tube 328 has a length that is larger than middle shield tube 334 and shorter than outer shield tube 332.

As seen in FIGS. 9A, 9B and 9D, MHR shield tube assembly 324 further includes a shield collar 326 at least partially disposed within a first end of outer shield tube 332. As seen in FIGS. 9D-9G, shield collar 326 includes a reduced diameter section 326a configured and dimensioned for insertion into outer shield tube 332 and an enlarged diameter section 326b configured and dimensioned for extension out of outer shield tube 332. A front end 326c of reduced diameter section 326a is configured and dimensioned for disposition between inner shield tube 328 and outer shield tube 332. Middle shielding tube 334, may be made from a suitable shielding material, e.g., lead.

In addition, a plurality of radio-transparent apertures or slots or slits 336, are located intermittently, and at a particular pitch, along the axial centerline in both the inner shield tube 328 and the middle shielding tube 334. The apertures or slots 336 are arranged so that when the MHR inner shield tube 328 and the lead MHR shielding tube 334 are disposed telescopingly arranged, and, in one embodiment, concentrically over the line source holder 308a, the line source 308 emits radioactivity substantially only through the apertures or slots 336. In one embodiment, the apertures or slots are arcuately-shaped. The MHR shield tube assembly 324 has an overall end-to-end length dimension designated as L3.

Figure 9:
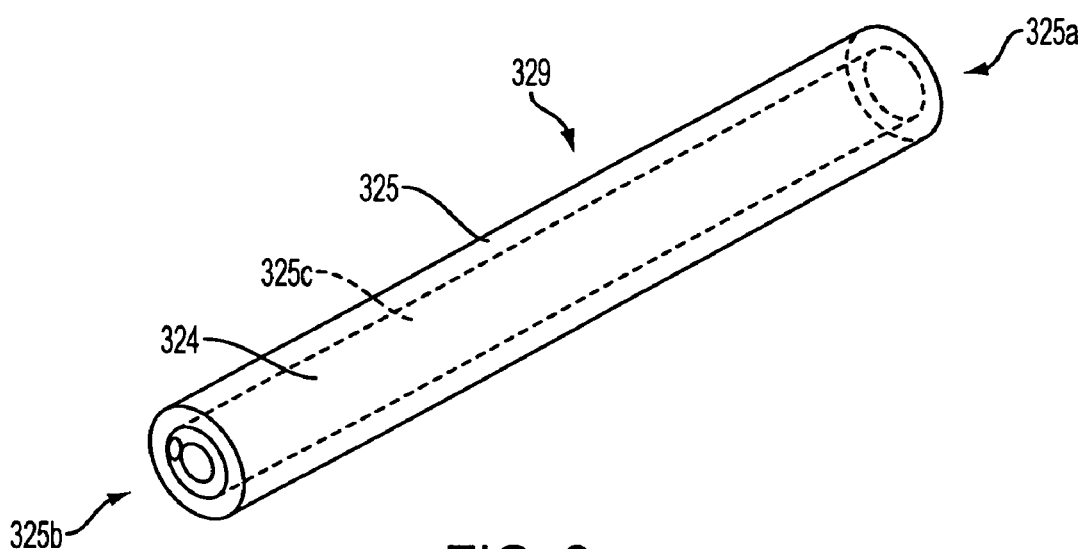
FIG. 9 is a perspective view of an MHR shield according to the present disclosure that includes an MHR shield assembly inserted inside an MHR shield assembly support tube.
Figure 9E:
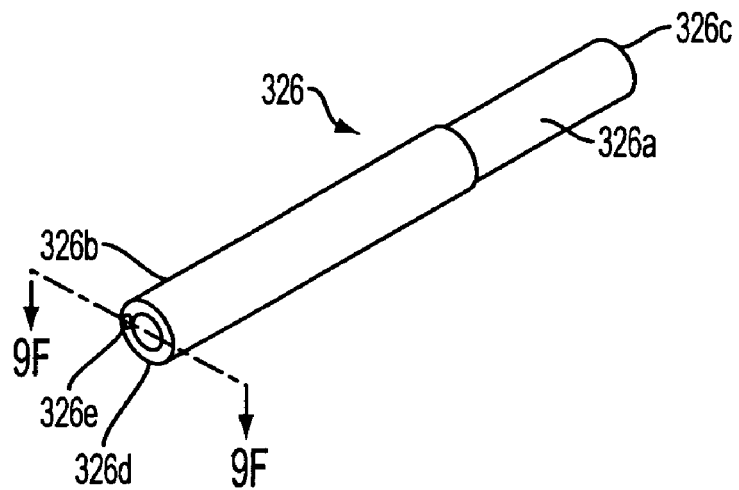
FIG. 9E is a perspective view of a portion of the MHR shield assembly of FIG. 9A.
Figure 9F:
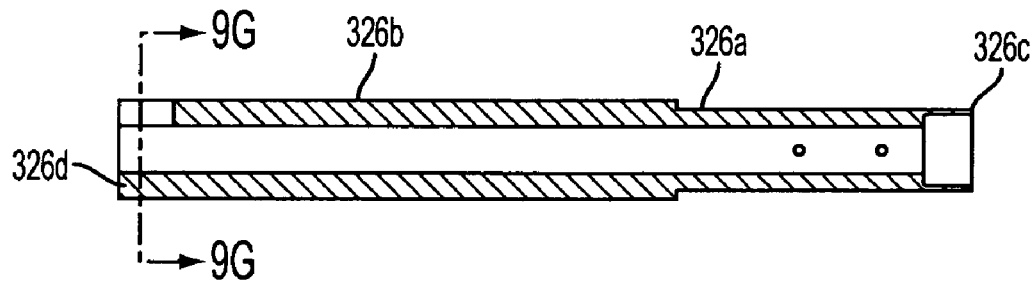
FIG. 9F is a cross-sectional view of the portion of the MHR shield assembly of FIG. 9A taken along section line 9F-9F of FIG. 9E.

As illustrated particularly in FIGS. 9D to 9G, the enlarged diameter section 326b of the shield collar 326 has a bore hole 326e formed in an end wall 326f of rear end 326d thereof. In one embodiment, bore hole 326e is longitudinally parallel to the axial centerline of the shield collar 326. The bore hole 326e will be discussed below in more detail with respect to the drive assemblies. As seen in FIGS. 9-9D, a front end 324c (see FIG. 9D of the MHR shield tube assembly 324 may be inserted into the rear end 325b of the MHR shield assembly support tube 325 to enable the MHR shield tube assembly 324 to slide inside the MHR shield assembly support tube 325. The MHR shield tube assembly 324 thereby may extend into, over or under the field of view or retract therefrom, as explained in more detail below with respect to FIG. 14.

Figure 10A:
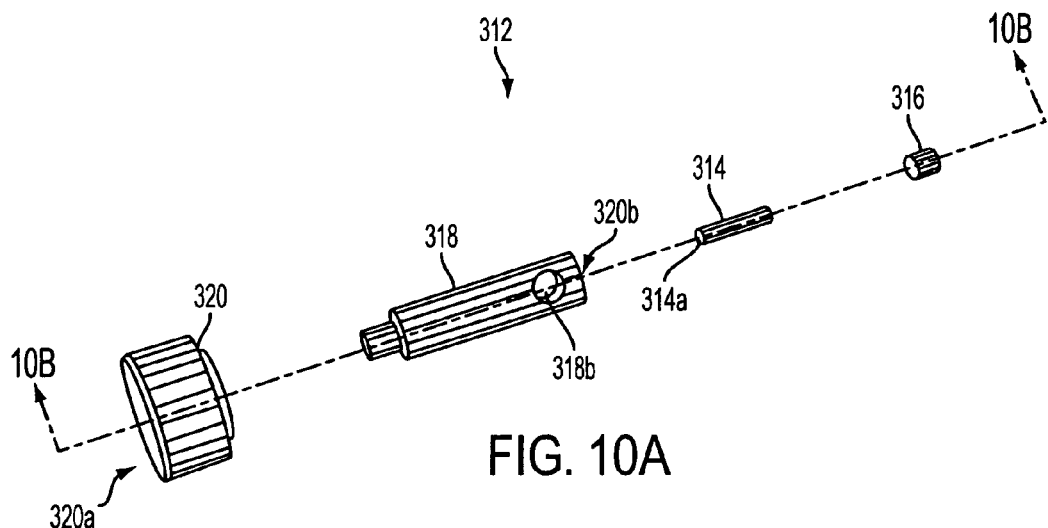
FIG. 10A is a perspective view of a point source assembly forming part of the AQCM of the present disclosure with parts separated.
Figure 10B:
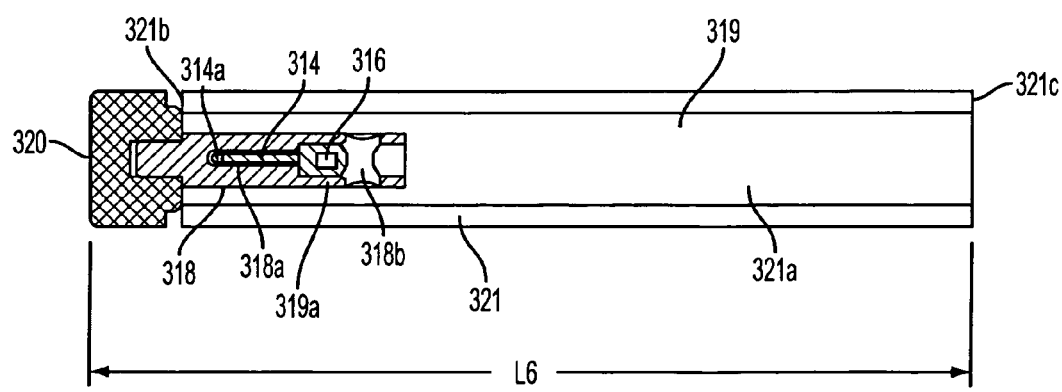
FIG. 10B is a cross-sectional view of the point source assembly of FIG. 10A taken along section line 10B-10B together with a cross-sectional view of a point source shaft and a point source holder tube.

Referring now to FIGS. 10A and 10B, the AQCM 300 also includes a point source assembly 312 having a partially hollow shaft or tube 318 defining a longitudinal bore hole 318a, a point source 314, having an active end 314a, disposed within bore hole 318a of tube 318, and a set screw 316 engageable with the bore hole 318a of bore tube 318. In one embodiment, the shaft or tube 318 is made from a metallic substance and a point source shielding plug 320 connected to an end of tube 318 opposite bore hole 318a. The point source shield plug 320 may be used for installing or replacing the point source 314 as periodically required due to radioactive decay or other needs. The point source 314 is made from a suitable radioactive material, e.g., a point source having an activity of 50 μCi (50 microcuries). In one embodiment, the bore hole 318a may be formed along the longitudinal centerline of the tube 318.

The tube 318 may also include a second bore hole 318b that is formed therein and at least partially intersecting, and, in one embodiment, substantially transversely to the first bore hole 318a. The first bore hole 318a receives the set screw 316, thereby enabling the point source 314 to be sealed by the set screw 316 within first bore hole 318a.

As seen in FIG. 10B, a rear end 320b of the point source assembly 312 is inserted into a bore 319a of a point source holder shaft 319. The point source assembly 312 and the point source holder shaft 319 are configured to be inserted into an interior region 321a of a point source support tube 321 having a front end 321b and a rear end 321c in a manner such that the front end 320a of the point source assembly 312 and the point source holder shaft 319 can be slid out of and away from the front end 321b of the point source support tube 321 and thereby extended into, under or over or retracted from the field of view, as discussed in more detail below with respect to FIG. 15. The point source holder shaft 319 and the point source shield plug 320 have a combined overall length dimension L6.

Figure 7:
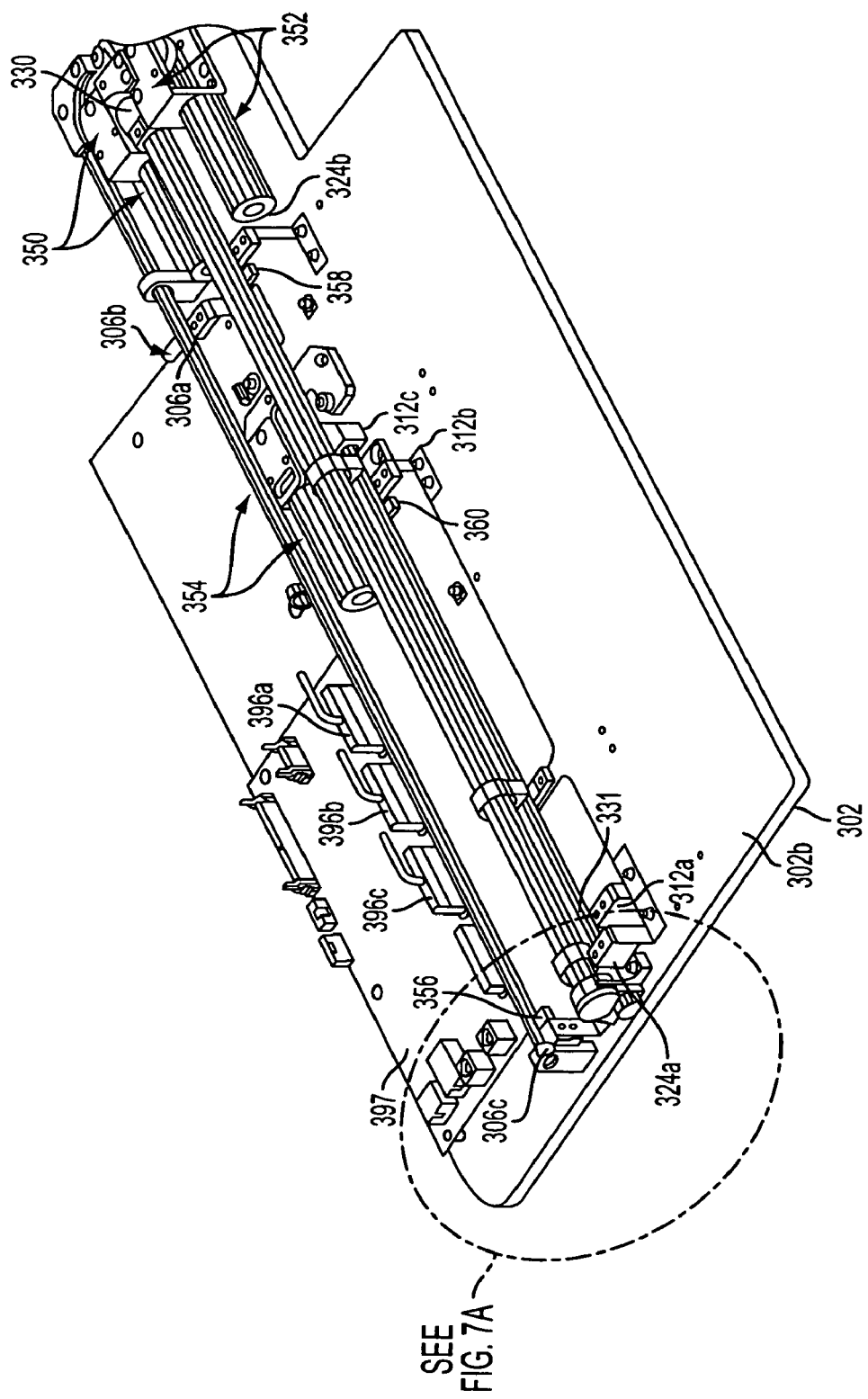
FIG. 7 is a further perspective view of the AQCM of FIG. 4 with some parts omitted.
Figure 7A:
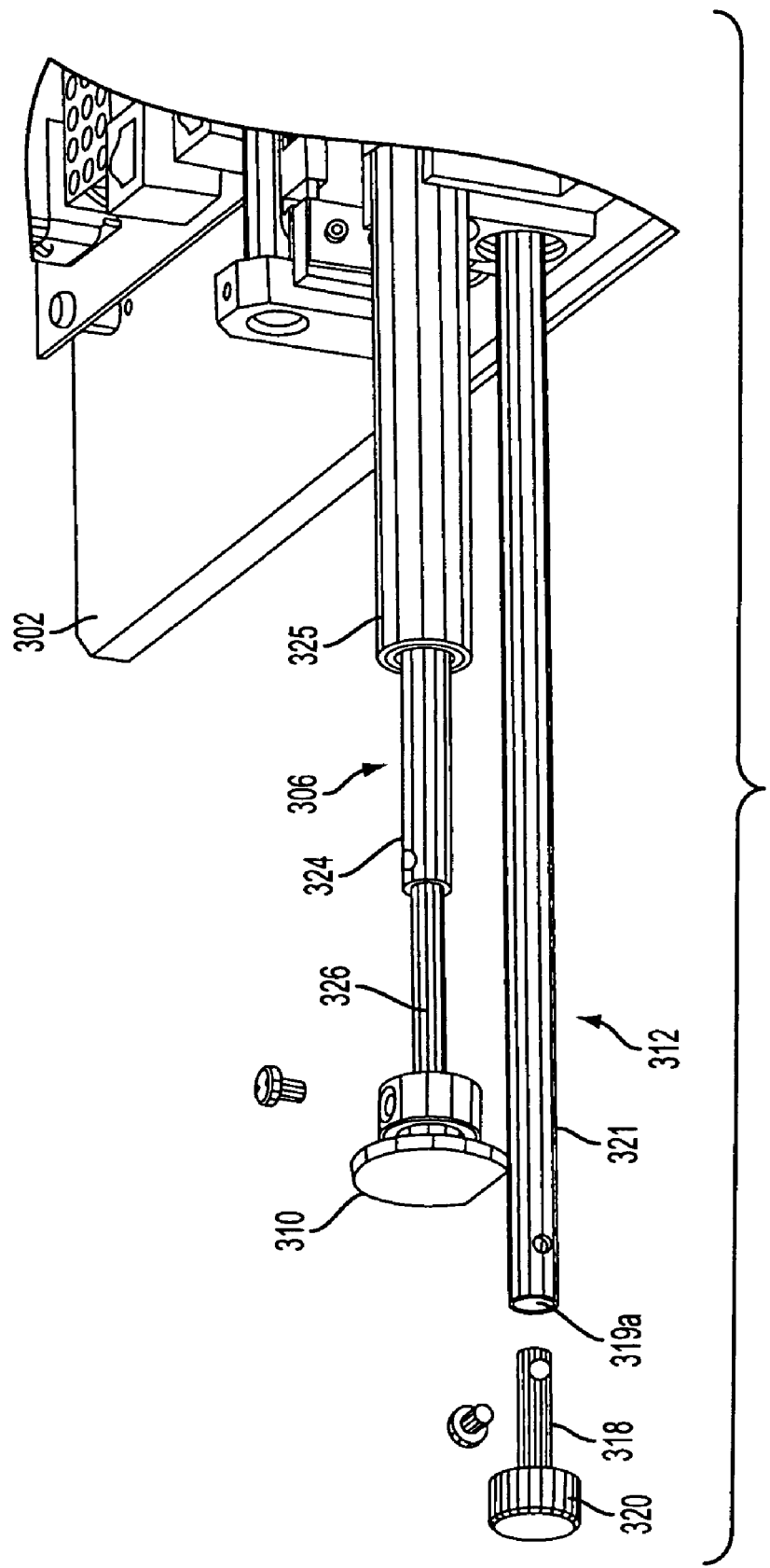
FIG. 7A is a perspective view of the AQCM with the line source assembly and MHR shield tube at least partially extended and with the point source assembly at least partially extended.

Referring back to FIGS. 4-7A, FIGS. 4 and 5 illustrate the AQCM 300 showing the second surface 302b of the mounting plate 302 on which are mounted substantially all of the components of the AQCM 300. The AQCM 300 includes a shield cover 400 which is lined with or made from a shielding material. The shielding components are described in more detail below. FIG. 7 is also a perspective view of the AQCM 300 showing the second surface 302b of the mounting plate 302 but without shield cover 400. More particularly, referring to FIGS. 4 to 7A, the planar surface 302b has mounted thereupon an extend/retract drive assembly 322. The extend/retract drive assembly 322 includes a first flexible gear assembly 370a that is configured to extend and retract the line source assembly 306 into and out of the field of view, as discussed below with respect to FIG. 13. The extend/retract drive assembly 322 further includes a second flexible gear assembly 370b that is configured to extend and retract the multiple head registration (MHR) shield tube assembly 324 from the line source assembly 306 when the line source 308 is extended into, over or under the field of view, as discussed below with respect to FIG. 14. The extend/retract drive assembly further includes a third flexible gear assembly 370c for driving the point source assembly 312 into, over or under the field of view, as discussed below with respect to FIG. 15.

In conjunction with the extract/retract drive assembly 322, the line source assembly 306 and the associated MHR shield tube assembly 324, and the point source assembly 312 are mounted on the surface 302b generally parallel to one another such that the line source 306 and the point source 312 may each be extended linearly from the rear end portion 210 of the PHS 200.

Referring particularly to FIGS. 5 to 7A, the first flexible gear assembly 370a provides motive power via a flexible gear set 372 that drives the line source assembly 306. As seen in FIG. 6A, the flexible gear set 372 includes a bevel driven gear 376b which is driven by a bevel pinion gear 376a that in turn, as explained in more detail below, is driven by motors 381a for the line source assembly 306. The flexible gear set 372 may include at least one drive spur gear 374a and a flexible gear rack 374b, with inner side 375a and outer side 375b and having a first end 371a, operatively coupled to line source holder tube 308a. A second end 373a of flexible gear rack 374b for the line source assembly 306 may be inserted inside a flexible gear rack guide means for line drive 350 such as flexible gear rack guide tube 382a for the line source assembly 306. The flexible gear rack 374b may be made from a flexible material such as plastic.

The second flexible gear assembly 370b provides motive power also via flexible gear set 372 that drives the MHR shield tube assembly 324. The flexible gear set 372 includes the bevel driven gear 376b which is driven by the bevel pinion gear 376 that in turn, as explained in more detail below, is driven by motor 381b for the MHR shield tube assembly 324. The flexible gear set 372 again may include the at least one drive spur gear 374a and the flexible gear rack 374b with inner side 375a and outer side 375b but having a first end 371b now operatively coupled to MHR shield tube assembly 324. A second end 373b of flexible gear rack 374b for the MHR shield tube assembly 324 may be inserted inside a flexible gear rack guide means for MHR drive 352 such as flexible gear rack guide tube 382b for the MHR shield tube assembly 324. Again, the flexible gear rack 374b may be made from a flexible material such as plastic.

The third flexible gear assembly 370c provides motive power via the flexible gear set 372 that drives the point source assembly 312. The flexible gear set 372 includes the bevel driven gear 376b which is driven by the bevel pinion gear 376 that in turn, as explained in more detail below, is driven by motor 381c for the point source assembly 312. The flexible gear set 372 may again include the at least one drive spur gear 374a and the flexible gear rack 374b with inner side 375a and outer side 375b but now having a first end 371c operatively coupled to point source holder 314. A second end 373c of flexible gear rack 374b for the point source assembly 312 may be inserted inside a flexible gear rack guide means for point drive 354 such as flexible gear rack guide tube 382c for the point source assembly 312. As before, the flexible gear rack 374b may be made from a flexible material such as plastic.

The drive spur gear 374a and the bevel driven gear 376b are commonly mounted in parallel on a shaft or axle 378. The bevel driven gear 376b and the drive spur gear 374a each include shaft extensions 376e and 374e, respectively, which enable fastening of the bevel driven gear 376b and the drive spur gear 374a to the shaft or axle 378 via fastening means such as, for example, set screws.

Referring particularly also to FIGS. 6C and 6D, a support structure, by way of example only and not limited thereto, may be a generally U-shaped housing 380 that includes a first arm 380a, a base 380c, and a second arm 380b parallel to the first arm 380a, wherein the first and second arms 380a and 380b are operatively connected to the base 380c to form the generally U-shaped configuration of the housing 380. The axle 378 (not shown in FIGS. 6C and 6d) extends vertically through an aperture 388 in the first arm 380a and extends through an axle housing 377 to the second arm 380b wherein the axle 378 is supported by bearings 390 disposed at the second arm 380b. The bevel pinion gear 376a is mounted on a motor shaft 383 that is driven by the motor 381a, 381c, or 381b, as applicable. The bevel pinion gear 376a interfaces with the bevel driven gear 376b thereby to drive the drive spur gear 374a.

Referring back to FIGS. 6A and 6B, the drive spur gear 374a has teeth 374c that interface with teeth 374d that are disposed on an inner side 375a of the flexible gear belt 374b. Idler rollers 394 are mounted on the second surface 302b of the mounting plate 302 such that the outer side 375b of the flexible gear belt 374b is retained by the rollers 394 while the teeth 374d on the inner side 375a interface with the drive spur gear teeth 374c. A flexible gear guide 395 is disposed with respect to the outer side 375b so as to guide and limit the motion of the flexible gear belt 374b with respect to the drive spur gear 374a and the flexible gear guide tube 382.

As illustrated particularly in FIG. 6C, the spur drive gear 374a is oriented such that shaft extension 374e for spur drive gear 374a and shaft extension 376e for bevel driven gear 376b for flexible gear assembly 370b of MHR shield tube assembly 324 are interfacing one another in support housing 380 such that the spur gear teeth 374c are substantially adjacent to the second arm 380b. In contrast, as illustrated particularly in FIG. 6D, for the flexible gear assemblies 370a and 370c for the line source assembly 306 and the point source assembly 312, respectively, the spur drive gear 374a is oriented such that shaft extension 374e for the spur gear drive 374a interfaces the second arm 380b rather than the shaft extension 376e for the bevel driven gear. As result, although distance h1 between the first and second support arms 380a and 380b, respectively, may be the same for the first, second and third flexible gear drive assemblies 370a, 370b and 370c, respectively, distance h2 between the plane of the spur drive gear teeth 374c and the first support arm 380a for the first and third flexible gear drive assemblies 370a and 370c, respectively, is less than distance h2' between the plane of the spur gear drive teeth 374c and the first support arm 380a for the second flexible gear drive assembly 370b. Therefore, when first and second flexible gear drive assemblies 370a and 370b are disposed side by side, as illustrated in FIG. 6B, the plane of the spur drive gear teeth 374c of the second flexible gear drive assembly 370b for the MHR shield tube assembly 324 is above (or below depending on the overall orientation of the AQCM 300) the plane of the spur drive gear teeth 374c of the first and third flexible gear drive assemblies 370a and 370c for the line and point drive source assemblies 306 and 312, respectively.

Referring now to FIGS. 6E, 6F and 6G, and in conjunction with previously discussed FIGS. 8A through 10B, the difference in height between h2 and h2' allows the end 371b of the flexible gear drive rack 374b for the MHR shield assembly 324 to be inserted into bore hole 326e formed in the wall 326f of the shield collar 326 (see FIG. 9F) at a height that is above (or below as explained previously) the flexible gear drive rack 374b for the line source assembly 306 or the line source assembly 312. As illustrated in FIG. 6E, the end 371b of the flexible gear drive rack 374b, upon insertion into bore hole 326e, may be fastened to the MHR shield tube assembly 324 with fastening means such as set screw 387b. Similarly, as illustrated in FIG. 6F, the end 371a of the flexible gear drive rack 374b may be fastened to the line source assembly 306 with similar fastening means such as set screw 387a. As illustrated in FIG. 6G, the end 371c of the flexible gear drive rack 374c may be fastened to point source holder shaft 319 of the point source assembly 312 with similar fastening means such as set screw 387c.

Figure 4:
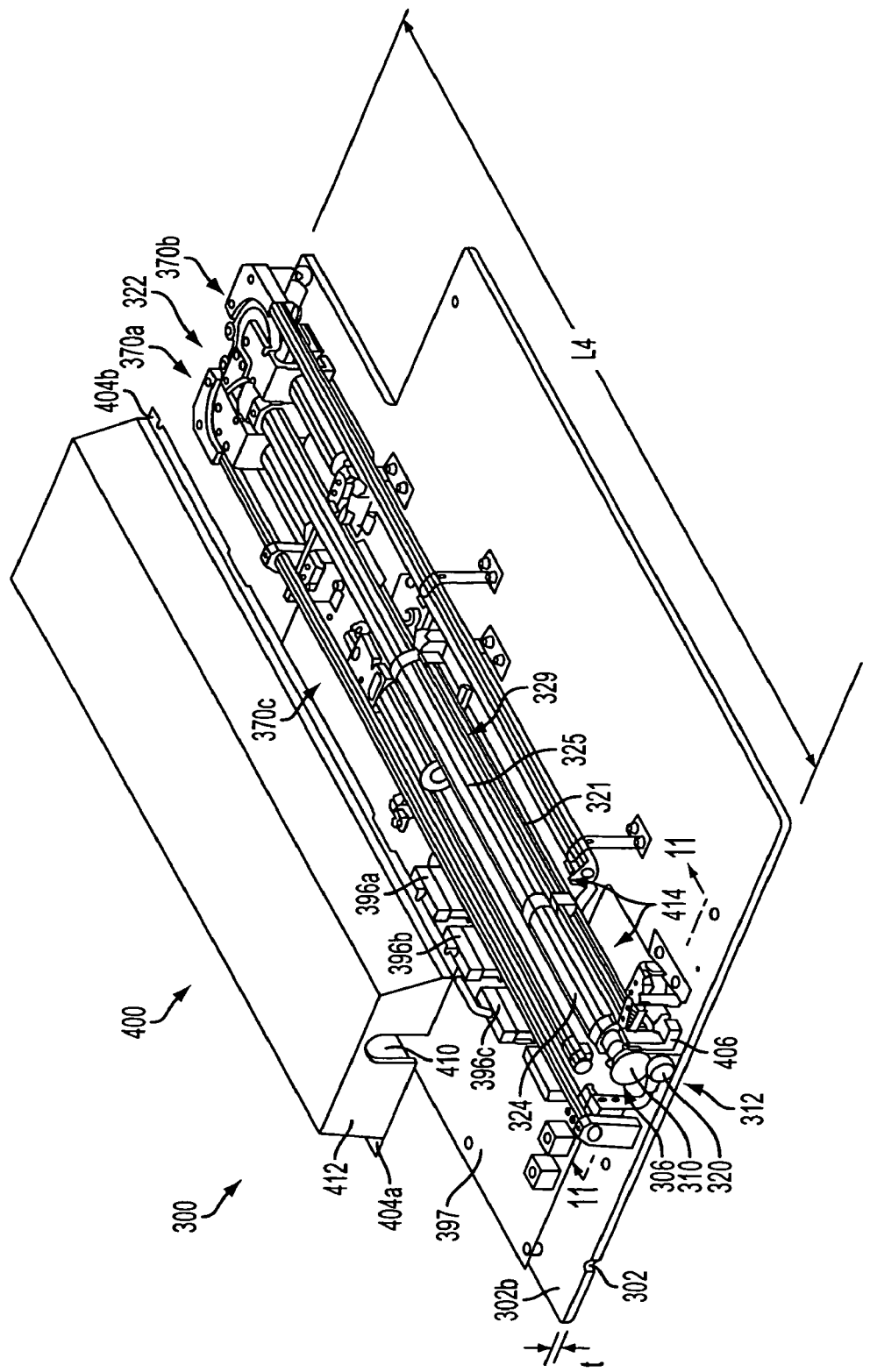
FIG. 4 is a bottom perspective view of the AQCM as mounted on a mounting frame on the underside of the patient handling system with a shield cover separated.
Figure 5:
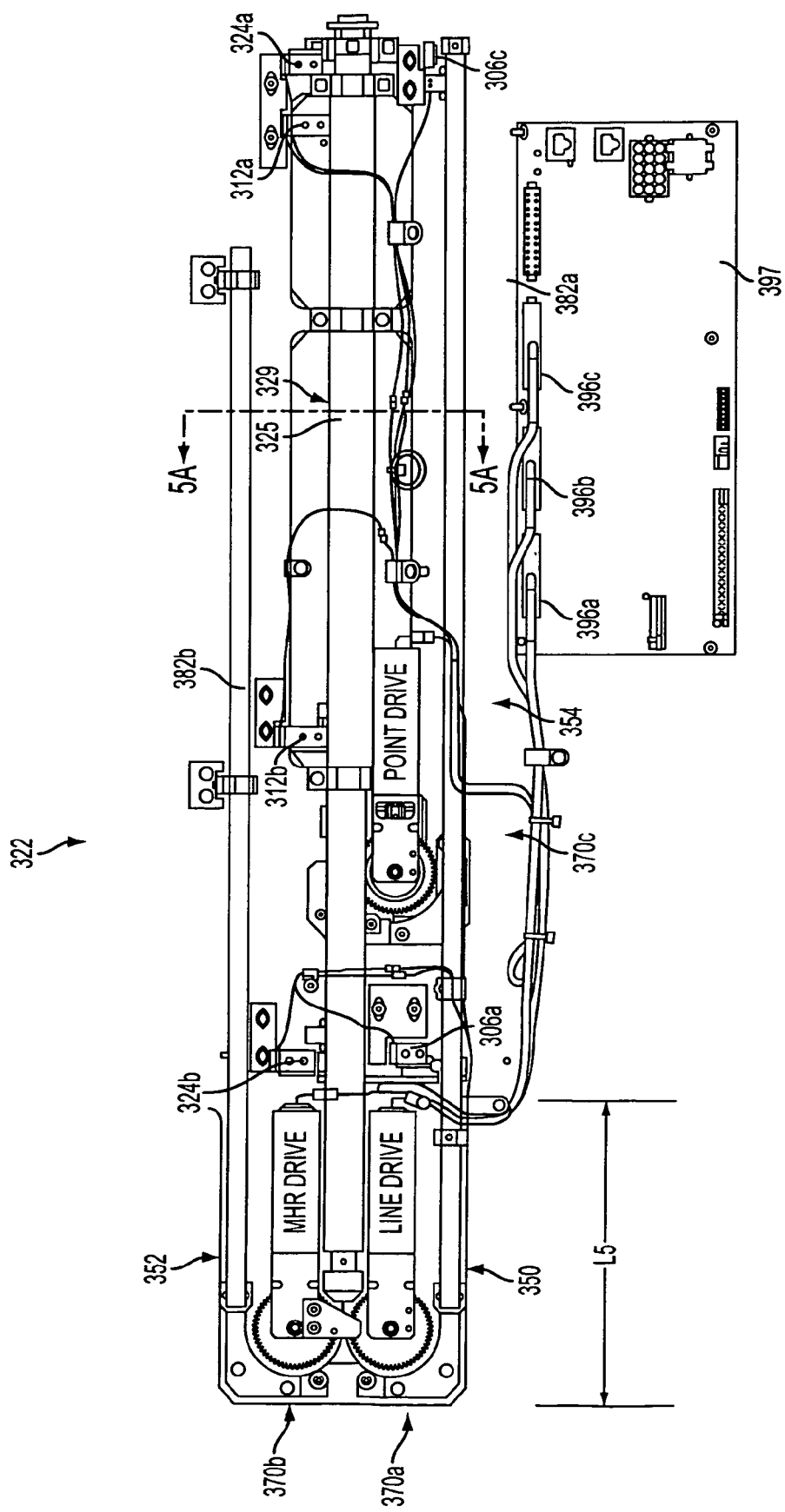
FIG. 5 is a plan view of the AQCM as mounted on the mounting frame on the underside of the patient handling system with the shield cover omitted.
Figure 5A:
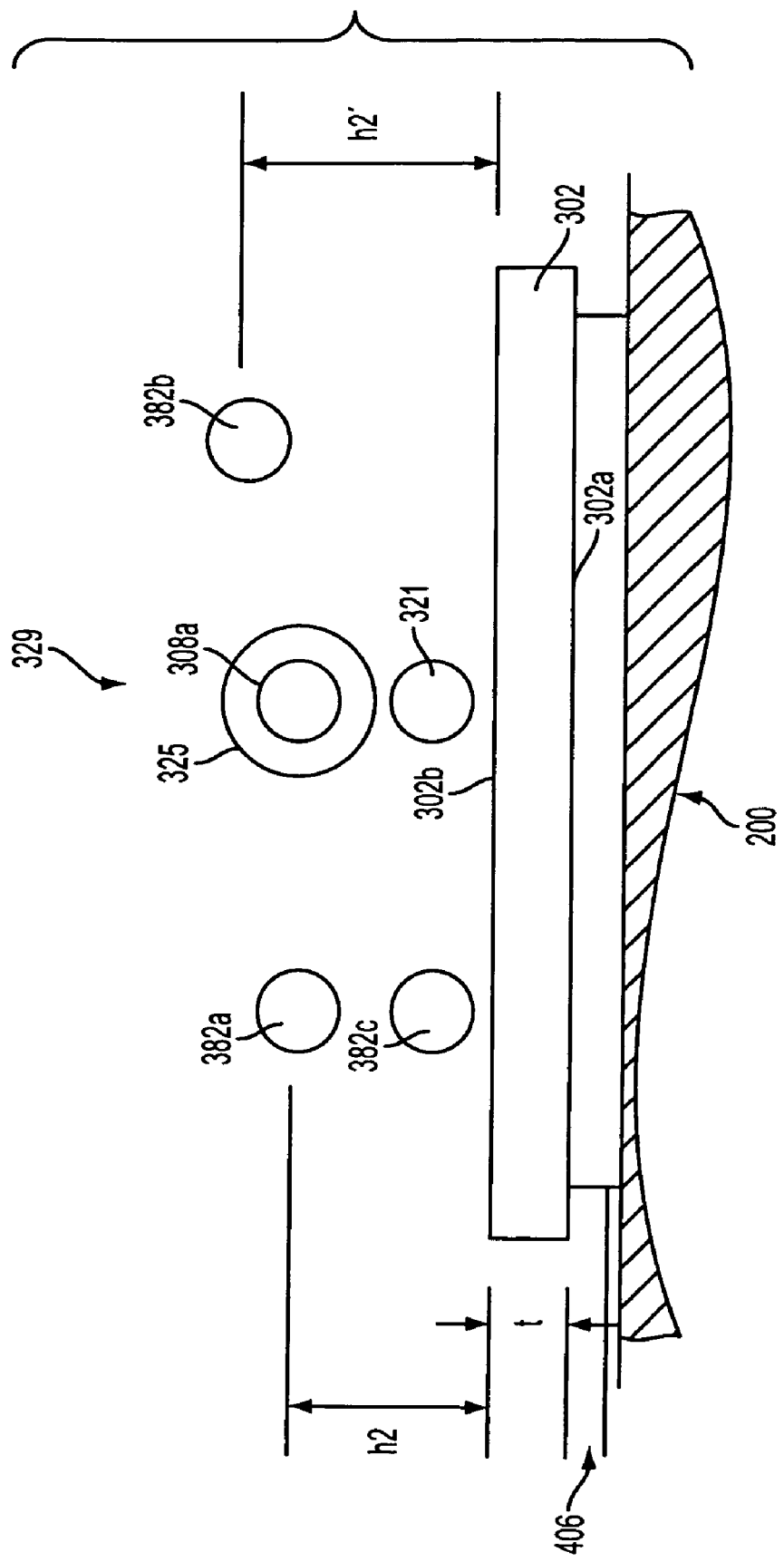
FIG. 5A is a cross-sectional elevation view of the AQCM of FIG. 5 taken along section line 5A-5A of FIG. 5.
Figure 6A:
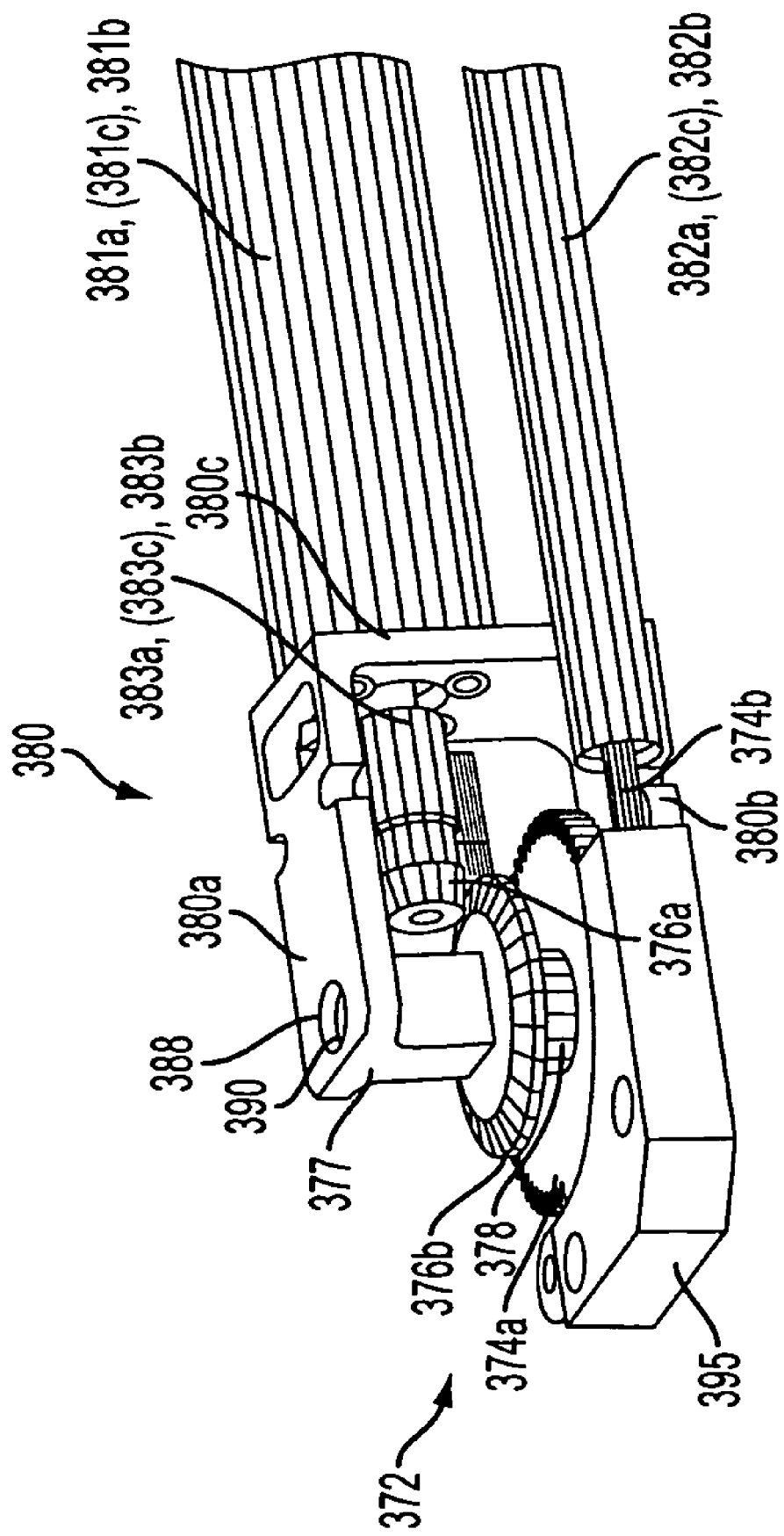
FIG. 6A is perspective view of a portion of a flexible gear drive assembly for a source assembly of the AQCM.

Referring to FIGS. 4, 5 and 5A, the point source holder tube 321 and the third flexible gear assembly 370c, including the flexible gear rack guide tube 382c for the point source assembly 312, are mounted directly proximate to the second surface 302b of the mounting plate 302. In one embodiment, directly above (or below as previously discussed) the point source holder tube 321 and the third flexible gear assembly 370c are mounted the first flexible gear assembly 370a, including the flexible gear rack guide tube 382a for the line source assembly 306, the MHR shield 329, which includes the MHR shield assembly support tube 325 and the MHR shield tube assembly 324, and at least the line source 308 and the line source holder tube 308a, and the second flexible gear rack guide tube 382b for the MHR shield tube assembly 324. The AQCM 300 is mounted on the surface 302b at appropriate locations by fastening means such as mounting brackets or other suitable means.

As related to the discussion above with respect to FIGS. 6C and 6D, those skilled in the art will recognize that, and understand how, the difference in height between h2 and h2' allows second flexible gear rack guide tube 382h for the MHR shield tube assembly 324 to be positioned above (or below as described above) the first flexible gear rack guide tube 382a, and also how end 371b is operatively coupled to MHR shield tube assembly 324 to be positioned above end 371a of the flexible gear drive rack 374b for the line source assembly 306 so that the MHR shield assembly 324 can be driven independently of the line source assembly 306. As discussed in more detail below with respect to FIG. 15, in that the point source assembly 312 has a shorter required travel extension as compared to the required travel extension of the line source assembly 306 and that of the MHR shield 329, the third flexible gear assembly 370c for the point source assembly 306 may be disposed on the surface 302b in a position closer to the front end portion 216 of the PHS 200 as compared to the position of the first and second flexible gear assemblies 370a and 370b, respectively. Those skilled in the art will recognize that, and understand how, the third flexible gear assembly 370c may be oriented to be disposed on the surface 302b on either side of the MHR shield 329. The embodiments are not limited in this context.

As particularly illustrated in FIGS. 4, 5 and 7, the AQCM 300 may further include a plurality of low voltage amplifiers 396a, 396b and 396c that are electrically coupled to the line drive 350 (e.g., drive motor 381a), to the MHR drive 352 (e.g., drive motor 381b) and to the point drive 354 (e.g., drive motor 381c), respectively, and which supply power from an electrical power source (not shown) to actuate the line source assembly 306, the MHR shield tube assembly 324 and the point source assembly 312. The AQCM 300 also includes control circuitry such as, for example but not limited to, a printed circuit board 397 to operate and control the actions of the AQCM 300 via the low voltage amplifiers 396a, 396b and 396c.

Figure 13:
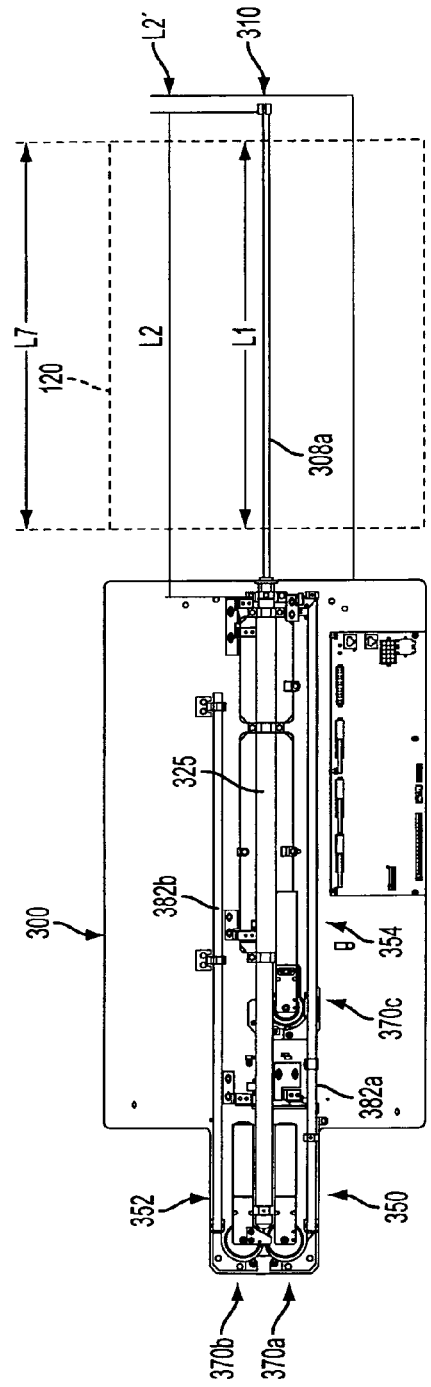
FIG. 13 is a plan view of the AQCM of the present disclosure with the line source assembly in the fully extended position in the field of view of a nuclear camera.

Referring now to FIGS. 12-15, FIG. 12 illustrates the AQCM 300 with the source assemblies 306 and 312 and the MHR shield tube assembly 324 in a fully retracted position over the mounting surface 302b. FIG. 13 illustrates the AQCM 300 with the line source assembly 306, more particularly the line source 308, in a fully extended position generally corresponding to the length L2 along the centerline axis of the line source holder tube 308a in a direction given by arrow A. The line source assembly 306 thereby has a travel distance substantially equal to the length L2 plus length L2' of the shielding plug 310 (see also FIGS. 8A and 8C). The line source 308 is positioned in the line source holder tube 308a such that active length L1 generally aligns with length L7 of field of view 120 of the nuclear camera system 101. In one embodiment, the length L2 is about 57.1 centimeters (about 22.5 inches). The active length L1 is about 38.7 centimeters (about 15.25 inches) and is generally centered alone the length L2.

FIG. 14 illustrates the AQCM 300 with the MHR shield tube assembly 324 in a fully extended position. As described above with respect to FIG. 9B, the plurality of radio-transparent apertures or slots or slits 336, in one embodiment the apertures or slots 336 may be arcuately-shaped, and may be located intermittently, and at a particular pitch, along the axial centerline in both the MHR inner shield tube 328 and the lead MHR shielding tube 334. The MHR shield tube assembly 324 has an overall end-to-end length dimension designated as L3 (see FIG. 9B). The apertures or slots or slits 336 are arranged so that when the MHR inner shield tube 328 and the MHR middle shield tube 334 are telescopically disposed and, in one embodiment, concentrically over the line source holder 308a, the line source 308 emits radioactivity substantially only through the apertures or slots or slits 336, and partially exposes the line source assembly 306 in the field of view 120 of the nuclear camera system 101 along the length L7. In one embodiment, the MHR inner shield tube 328 and the MHR middle shield tube 334 have five apertures or slots having a width of about 0.2 centimeters (about 0.080 inches) and a pitch of about 7.462 centimeters (about 2.938 inches) except for the first aperture or slot nearest to the front end 323a, which may have a distance from the front end 323a of about 7.71 centimeters (about 3.035 inches). The time to move by remotely and automatically extending into, over or under the field of view 120 or to move by remotely and automatically retracting from the field of view 120 the line source assembly 306 and move by extending or retracting the MHR shield tube assembly 324 into, over or under or from the field of view 120, respectively, may be about 1.2 seconds.

FIG. 15 illustrates the AQCM 300 with the point source assembly 312 in a fully extended position. More particularly, the point source support tube 321 (see FIG. 10B) is remotely and automatically extended into, over or under the field of view 120 of the nuclear camera system 101 and remotely and automatically retracted therefrom. In one embodiment, the position of the PHS 200 is adjusted such that the point source 314 (see FIG. 10A) is automatically extended into, over or under the field of view 120 such that the point source 314 is substantially centered in the field of view 120, and particularly, the point source 314 is extended over a travel distance L6 of about 33.66 centimeters (about 13.25 inches) with the PHS 200 adjusted so that the point source 314 extends about midway into the field of view 120 along the length L7 or about 19.37 centimeters (about 7.125 inches). The time to move by automatically and remotely extending the point source assembly 312 into, over or under the field of view 120 or automatically and remotely retracting the point source assembly 312 from the field of view 120, may be about seven (7) seconds.

Referring back to FIGS. 4, 5 and 7, the actions and movements of the AQCM 300 are at least partially controlled by extend limit switch 306a for line source 308, extend mechanical stop 306b for line source extend, retract limit switch 306c for line source 306, and common line and MHR retract mechanical stop 330 for line source 306 and MHR shield tube 324, each of the foregoing being mounted on the surface 302b to effect, in conjunction with the control circuitry 397 and voltage amplifiers 396a and 396b, the above-described automatic extension and automatic retraction of the line source assembly 306 and the MHR shield tube assembly 324, respectively.

Also mounted upon the planar surface 302b are extend limit switch 324a for MHR shield tube assembly 324, common mechanical stop 331 for point source holder 314 and MHR shield tube assembly 324, retract limit switch 324b for MHR shield tube assembly 324, point extend limit switch 312a, point retract limit switch 312b, and point retract mechanical stop 312c, each of the foregoing being mounted on the surface 302b to effect, in conjunction with the control circuitry 397 and voltage amplifiers 396b and 396c, the above-described remote automatic extension and remote automatic retraction of the MHR shield tube assembly 324 and the point source assembly 312, respectively.

The surface 302b also includes mounted thereupon a line actuator bar 356 in general proximity to line retract limit switch 306c, an MHR actuator bar 358 in general proximity to MHR retract limit switch 324b, and point actuator bar 360 in general proximity to point retract limit switch 312h, each of the foregoing also being mounted on the surface 302b to effect, in conjunction with the control circuitry 397 and voltage amplifiers 396b and 396c, the above-described automatic extension and automatic retraction of the MHR shield tube assembly 324 and the point source assembly 312, respectively.

Figure 11:
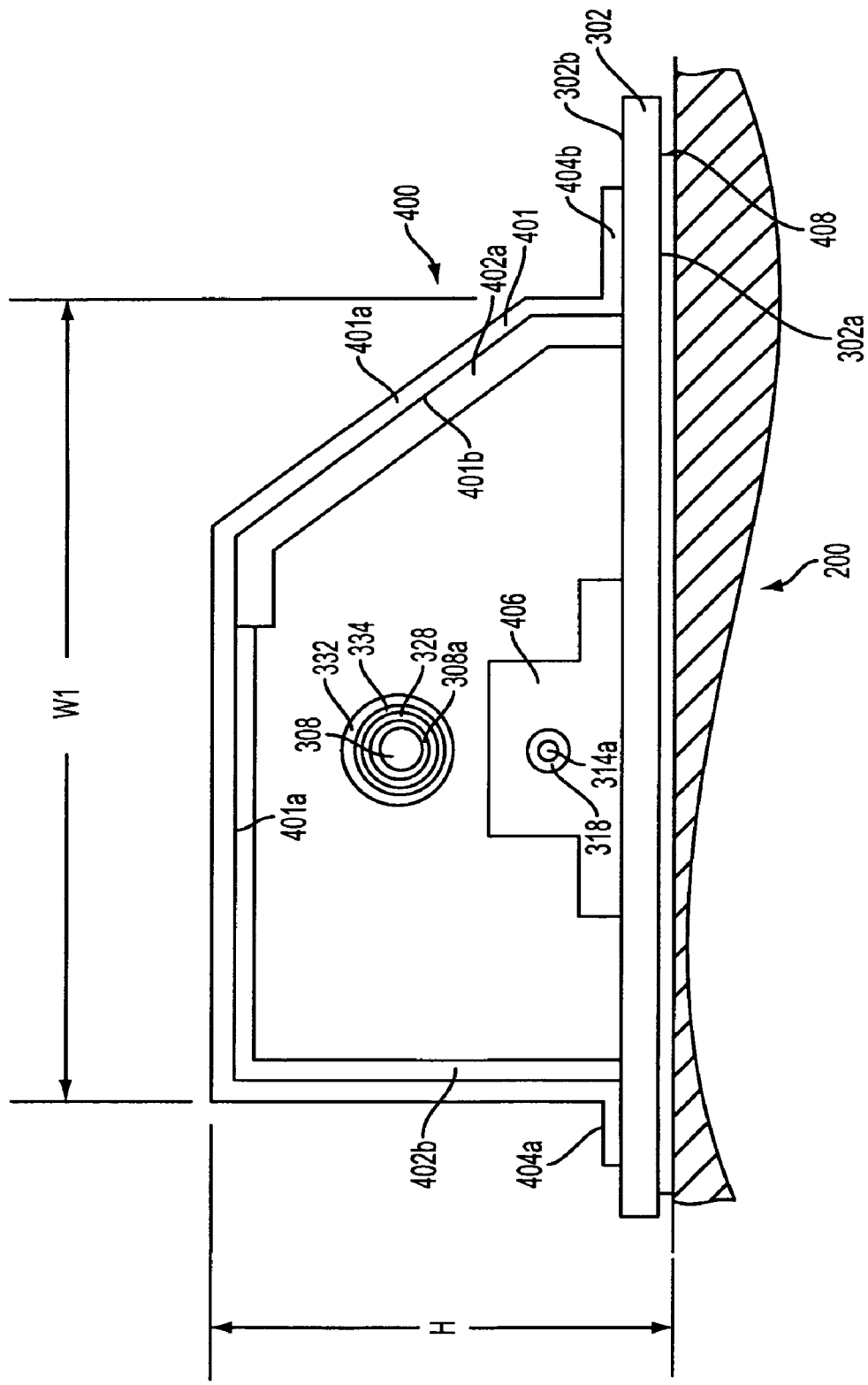
FIG. 11 is a cross-sectional view of the AQCM taken along line 11-11 of FIG. 4.
Figure 12:
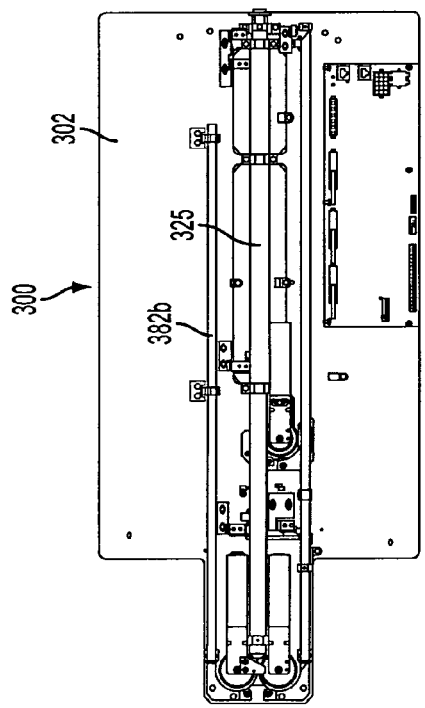
FIG. 12 is a plan view of the AQCM of the present disclosure with the source assemblies in the fully retracted position.

In conjunction with FIG. 11, FIG. 4 illustrates the AQCM 300, including shield cover 400, as mounted on the second mounting surface 302b of the mounting frame 302 on the underside of the PHS 200 with the shield cover 400 separated from the mounting plate 302. In FIG. 11, non-shielded components such as the line drive 350 (e.g., motor 381a), the MHR drive 352 (e.g., motor 381b) and the point drive 354 (e.g., motor 381c) and the flexible gear rack support tubes 382a, 382b and 382c, for example, are not shown. The shield cover 400 may have a sloped portion 401a and be formed from an outer sheet metal covering 401 having an inner surface 401b and having mounting flaps 404a and 404b that are each configured to interface with the second surface 302h of the mounting plate 302 for mounting the shield cover 400 to the mounting plate 302. The shield cover 400 may include first and second lead linings 402a and 402b each interfacing with inner surface 401b. The first lead lining 402a may be positioned generally along the sloped portion 401a and may have a greater thickness than second lead lining 402b. The shield cover 400 may include an aperture 410 provided in a front panel 412 of the outer covering 401 and configured to receive the point source holder support tube 321. A front shielding block 406, which also may be made from lead, is positioned at the aperture 410 and over the point source holder support tube 321. A lead plate 408 may be mounted on the first surface 302a of the mounting plate 302 to provide radiation protection to the patient "P" when positioned on the PHS 200 (see FIG. 2). Additionally, shielding inserts 414 may be inserted on the second surface 302b under the point source 314 and the line source 308 to provide further protection.

The line and point sources 308 and 314, respectively, are thus fully shielded when in the retracted position. The line and point sources 306 and 312 are generally intended to be fully retracted during any clinical study of a patient, so that radiation exposure to the patient from the AQCM 300 is considered to be negligible. Tamper resistant construction may be employed such as the use of "spanner head" screws to secure both the point source and the line source assemblies.

The configuration of the AQCM 300 with the described flexible gear assemblies 370a, 370b and 370c and the resulting method of extending and retracting the point source and the line source enables a low profile or reduced form factor. Referring to FIGS. 4 and 11, the envelope of the AQCM 400 is given by the dimensions height H of the shield cover 400, the width W1 of the shield cover, and the length L4 of the mounting plate 302 or approximately 5.72 centimeters (about 2.25 inches) high by approximately 15.24 centimeters (about 6 inches) wide by approximately 83.8 centimeters (about 33 inches) long, respectively. The low profile or reduced form factor facilitates and enables mounting of the AQCM 300 within the patient handling system 200. The compact overall size and dimensions of the AQCM 300 also minimize the amount of shielding required to shield the sources when the line source 306 and the point source 312 are fully retracted into their housing.

Referring to FIGS. 5 and 11, since the line source 306 and MHR shield tube assembly 324, in one embodiment, must be extended approximately 57.1 centimeters (about 22.5 inches) away from the front end portion 216 of the PHS 200 to be fully extended over the field of view 120 of the nuclear camera system detectors 110 and 112, and also must be rigidly supported on the mounting plate 302 and contained within the shield cover 400, the first, second and third flexible gear assemblies 370a, 370b and 370c, respectively, are configured to fit within an approximate envelope of approximately 5.72 centimeters (about 2.25 inches) high (dimension H) by approximately 15.24 centimeters (about 6 inches) wide (dimension W1) by approximately 12.7 centimeters (about 5 inches) long (dimension L5), respectively.

Figure 8A:
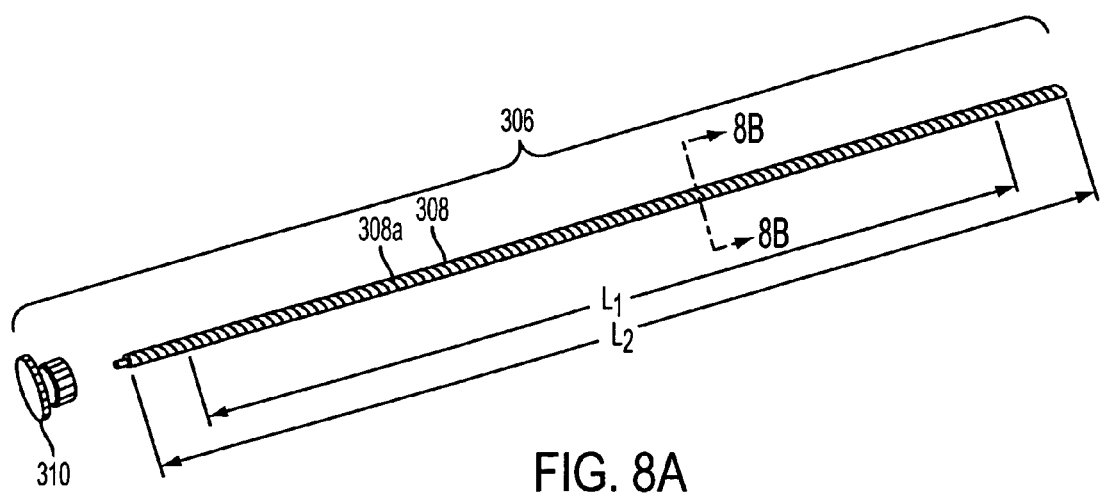
FIG. 8A is a perspective view of a line source assembly forming part of the AQCM of the present disclosure with parts separated.
Figure 8B:
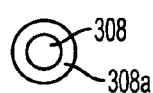
FIG. 8B is a cross-sectional view of the line source assembly of FIG. 5A as taken along section line 8B-8B of FIG. 5A.
Figure 8C:
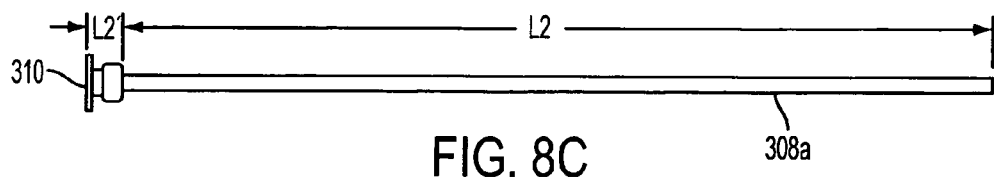

In one embodiment, to meet the foregoing size configuration requirements, referring to FIGS. 8A-8C, the line source holder 308a may be constructed of tubing having dimensions of about 0.375 inch diameter by about 0.058 inch wall thickness and made from 6063-T832 aluminum tubing. As previously mentioned, the line source 308 may be a 10 mCi line source housed in a tube 308a having an outside diameter of about 0.250 inches and length 12 of approximately 19 inches, wherein the tube 308a is hermetically sealed and made from stainless steel. The line source shield plug 310 may be used for installing or replacing the line source 308 as periodically required due to radioactive decay or other needs.

Figure 9G:
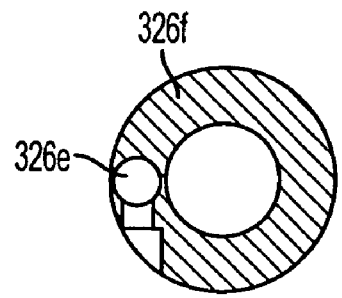
FIG. 9G is a cross-sectional view of the portion of the MHR shield assembly of FIG. 9F taken along section line 9G-9G of FIG. 9F.

Referring to FIGS. 9 to 9G, in one embodiment, the MHR shield 329 includes the hollow inner shield tube 328 having dimensions of 0.500 inches outer diameter by 0.058 inches wall thickness and that may be made from 6063-T832 aluminum tube. The MHR shield 329 also may include the outer shield tube 325 having dimensions of about 0.750 inches outer diameter by about 0.058 inches wall thickness and which may be made from 6063-TS32 aluminum tube. The MHR middle shield tube 334 may have dimensions of about 0.625 inches outer diameter by about 0.060 inches wall thickness and may be formed of a plurality of lead tube segments each approximately 3 inches long. The plurality of radiotransparent apertures or slots or slits 336 may be formed by 0.080 inch wide plastic washers that separate the shield tube 334 segments to create, as previously mentioned, the five apertures or slots having a width of about 0.2 centimeters (about 0.080 inches) and a pitch of about 7.462 centimeters (about 2.938 inches) except for the first aperture or slot nearest to the front end 323a, which may have a distance from the front end 323a of about 7.71 centimeters (about 3.035 inches). The MHR inner shield tube 328 slides over the line source mounting tube 308a. The MHR shield tube assembly 324 slides within the MHR shield assembly support tube 325 that may have dimension of an outer diameter of about 0.875 inches by about 0.058 inches wall thickness and that may be made from 6063-T832 aluminum support tube. Both the line source assembly 306 and the MHR shield tube assembly 324 may be secured as required with epoxy or other suitable bonding material.

Referring to FIGS. 10A to 10B, in one embodiment, the point source shaft 319 may have dimensions of about 0.375 inches outer diameter and may be made from steel. The point source shaft 319 may slide into and be supported within the point source support tube 321 which may have dimensions of about 0.500 inches outer diameter by about 0.058 inches wall thickness and which may be made from 6063-T832 aluminum tube.

As previously described, the point source 314 may be a 50 u.Ci source that is housed in the point source shaft or tube 318. The point source shaft or tube 318 may be made from stainless steel and may be formed as a hermetically sealed capsule having dimensions of about 2 millimeters outer diameter by about 10 millimeters in length.

Referring to FIGS. 4 and 5A, in one embodiment, the mounting frame 302 may made from 6061-T6 aluminum plate having a thickness "t" of about 0.312 inches.

In one embodiment, the outer sheet metal covering 401 of the shield cover 400 may be made from steel sheet metal and may have a thickness dimension of about 18 gauge (0.48 inches). The first and second lead linings 402a and 402b may have a thickness ranging from a minimum of about 0.125 inches to a maximum of about 0.250 inches and may be glued to the inner surface 401b of the outer sheet metal covering 401.

It is contemplated that the shielding inserts 414 may be inserted on the second surface 302b under the point source 314 and the line source 308 to provide further protection and may also be milled into pockets in the mounting plate 302 and may have a thickness of about 0.125 inches. It is envisioned that the front shielding block 406, and a rear shielding block (not shown) at the rear end portion of the AQCM 300, may have a thickness of about 0.500 inches.

In one embodiment, 18 gauge (0.048 inch) thick steel sheet metal brackets, lined with 0.125T" thick lead, seal the rear openings where the tubes go though the shield cover. Two additional 0.125 inch lead tubes wrap around the MHR support tube 325 in the area of the line source 306.

Referring to FIGS. 5, 5A, 6A to 6G, in one embodiment, the flexible gear assemblies 370a, 370b, 370c may include the housing 380 being made from 7075-T651 aluminum.

The motors 381a, 381b and 381 may be 24 volts direct current (VDC) motors, each with a steel gear mounting shaft 383a, 383b, or 383b, respectively. The gear axle 378 may be made from steel. The axle bearings 390 may be made from bronze. The bevel pinion gear 376a, the bevel driven gear 376b, the drive spur gear 374a, the flexible gear rack 374b, the idler rollers 394, the flexible gear guides 395, the flexible gear rack support tubes 382a, 382b and 382c and associated mounting hardware may be made from plastic.

It is envisioned that the flexible gear drive assemblies 370a, 370b and 370c are assembled as a single sub-assembly to control tolerance accumulation and to facilitate construction.

When installed to the PHS 200, the AQCM 300 utilizes the up/down motion of the PHS 200 to position vertically relative to the gantry/detectors of the nuclear camera system 101. Once vertical position is obtained, the AQCM 300 uses the flexible gear drive assemblies to axially position either the line source, the point source or the line source shield tube (MHR shield) within the camera detector field of view (FOV). The level of radioactivity and direction and orientation of the radioactivity as measured by the detectors 110 and 120 of the nuclear camera system 101 are compared to the known level of radioactivity and direction and orientation of the radioactivity provided by the line source and the point source to yield the calibration results. The configuration of the AQCM is such that other apparatuses may be installed on or near the PHS, such as an Integrated Collimator Changer (ICC) for example.

During operation of the nuclear camera system 101 with patient "P", the AQCM 300 is in a fully retracted and shielded configuration such that the patient "P" receives no significant radioactive dose from the AQCM 300. Those skilled in the art will recognize that, and understand how, the AQCM 300 may be integrated with nuclear camera systems having alternative designs of patient beds or patient handling systems as compared to the PHS 200 illustrated herein. The embodiments are not limited in this context.

Although the present invention has been described in accordance with the embodiments shown, one of ordinary skill in the art will readily recognize that there could be variations to the embodiment and these variations would be within the spirit and scope of the present invention. Accordingly, many modifications may be made by one of ordinary skill in the art without departing from the spirit and scope of the appended claims.

What is claimed is:

1. A quality control mechanism for a nuclear camera system having a field of view, the quality control mechanism comprising:
    at least one source assembly for a radioactive material wherein the at least one source assembly is configured with respect to the quality control mechanism in order to automatically remotely move the radioactive material into the field of view and automatically remotely move the radioactive material out of the field of view, wherein the radioactive material is configured for being imaged at a first time for automatically calibrating the nuclear camera system and for being retracted and non-imageable at a second time during a patient imaging operation by the nuclear camera system.

2. A quality control mechanism according to claim 1, wherein the nuclear camera system comprises a patient handling system having a front end and a rear end and wherein the quality control mechanism is integrated with the patient handling system at the front end such that the radioactive material can be at least one of automatically remotely extended into the field of view and automatically remotely retracted from the field of view.

3. A quality control mechanism according to claim 2, wherein the at least one source assembly is mounted on a mounting plate and wherein the quality control mechanism is integrated with the patient handling system via the mounting plate being mounted to the patient handling system.

4. A quality control mechanism according to claim 3, wherein the at least one source assembly comprises a line source assembly having a line source incorporated therein, wherein the line source is a radioactive material.

5. A quality control mechanism according to claim 4, further comprising a line drive for driving the line source by at least one of extending the line source into the field of view and retracting the line source from the field of view.

6. A quality control mechanism according to claim 4, further comprising a multiple head registration assembly configured with a plurality of slots formed therein and configured to extend over and shield the line source assembly such that the line source emits a field of radiation substantially only through the plurality of slots.

7. A quality control mechanism according to claim 3, wherein the at least one source assembly comprises a point source incorporated therein wherein the point source is a radioactive material.

8. A quality control mechanism according to claim 7, further comprising a point drive for driving the point source by at least one of extending the point source into the field of view and retracting the point source out of the field of view.

9. A quality control mechanism according to claim 1, further comprising a shield cover configured to shield the radioactive material.

10. A quality control mechanism according to claim 5, wherein the line drive comprises:
    a flexible gear set including:
    a drive gear; and
    a flexible gear rack interfacing with the drive gear, the flexible gear rack operatively connected to the line drive to enable at least one of the extension and retraction of the line source to and from the field of view.

11. A quality control mechanism according to claim 8, wherein the point drive comprises:
    a flexible gear set including:
    a drive gear; and
    a flexible gear rack interfacing with the drive gear, the flexible gear rack operatively connected to the point drive to enable at least one of the extension and retraction of the point source to and from the field of view.

12. A quality control mechanism according to claim 6, wherein the multiple head registration assembly comprises:
    a multiple head registration assembly shield tube; and
    a drive for driving the multiple head registration assembly, the drive including:
    a drive gear; and
    a flexible gear rack interfacing with the drive gear, the flexible gear rack operatively connected to the multiple head registration assembly such that the plurality of slots can be extended over and shield the line source assembly such that the line source emits a field of radiation substantially only through the plurality of slots.

13. A quality control mechanism according to claim 12, wherein the drive of the multiple head registration includes a bevel pinion gear interfacing with a bevel driven gear.

14. A quality control mechanism according to claim 1, wherein an envelope of the quality control mechanism is defined by a height not greater than about 5.72 centimeters (about 2.25 inches), by a width not greater than about 15.24 centimeters (about 6 inches) and by a length not greater than about 83.8 centimeters (about 33 inches).

15. A method of automatically calibrating a nuclear camera system having a field of view, the method comprising the step of:
    at least one of automatically remotely extending into the field of view and automatically remotely retracting from the field of view a radioactive material, wherein the radioactive material is imaged prior to a patient imaging operation by the nuclear camera system.

16. A method of calibrating according to claim 15, wherein the radioactive material is configured as one of a line source and a point source.

17. A method of calibrating according to claim 15, wherein the radioactive material is configured as a line source, the method further comprising the step of:

extending a shield tube over the line source, the shield tube including a plurality of slits formed therein such that the line source emits a field of radiation substantially only through the plurality of slits.

* * * * *